(12) United States Patent
Yarra et al.

(10) Patent No.: US 12,167,842 B2
(45) Date of Patent: Dec. 17, 2024

(54) HANDLE AND CARTRIDGE SYSTEM FOR MEDICAL INTERVENTIONS

(71) Applicant: Teleflex Life Sciences LLC, Wilmington, DE (US)

(72) Inventors: Curtis Yarra, Oakland, CA (US); Christopher Zaler, Los Gatos, CA (US); Alexander Charles Gordon, San Carlos, CA (US); Erik Noel, San Ramon, CA (US); Calvin Lam, Dublin, CA (US); Kevin Alexander Lessard, San Francisco, CA (US); Jolene Cutts, San Francisco, CA (US); Maheshwara Rao, Oakland, CA (US)

(73) Assignee: Teleflex Life Sciences LLC, Wilmington, DE (US)

(*) Notice: Subject to any disclaimer, the term of this patent is extended or adjusted under 35 U.S.C. 154(b) by 187 days.

(21) Appl. No.: 17/384,056

(22) Filed: Jul. 23, 2021

(65) Prior Publication Data
US 2022/0031358 A1    Feb. 3, 2022

Related U.S. Application Data

(60) Provisional application No. 63/060,442, filed on Aug. 3, 2020.

(51) Int. Cl.
*A61B 17/00* (2006.01)
*A61B 17/04* (2006.01)
(Continued)

(52) U.S. Cl.
CPC .... *A61B 17/00234* (2013.01); *A61B 17/0401* (2013.01); *A61B 17/0467* (2013.01);
(Continued)

(58) Field of Classification Search
CPC ............ A61B 17/06; A61B 2017/0416; A61B 17/06066; A61B 17/0469; A61B 2017/0479; A61B 2017/0409; A61B 2017/047; A61B 17/06114; A61B 17/3468; A61B 2017/06095; A61B 17/00234;
(Continued)

(56) References Cited

U.S. PATENT DOCUMENTS

| 659,422 A | 10/1900 | Shidler |
| 780,392 A | 1/1905 | Wanamaker et al. |

(Continued)

FOREIGN PATENT DOCUMENTS

| CA | 2477220 | 11/2007 |
| CN | 101795641 A | 8/2010 |

(Continued)

OTHER PUBLICATIONS

Singapore Written Opinion mailed Jul. 5, 2022 in SG Patent Application No. 11202200716X.
(Continued)

*Primary Examiner* — Richard G Louis
(74) *Attorney, Agent, or Firm* — Dorsey & Whitney LLP

(57) ABSTRACT

An apparatus for transferring mechanical energy in a handle to a cartridge to manipulate tissue or anatomical structures within the body of a human or animal subject for the purpose of treating diseases or disorders.

4 Claims, 18 Drawing Sheets

(51) Int. Cl.
*A61B 17/06* (2006.01)
*A61B 17/34* (2006.01)

(52) U.S. Cl.
CPC .... *A61B 17/06114* (2013.01); *A61B 17/3468* (2013.01); *A61B 2017/00389* (2013.01); *A61B 2017/0409* (2013.01); *A61B 2017/06095* (2013.01)

(58) Field of Classification Search
CPC ............ A61B 17/0401; A61B 17/0467; A61B 2017/00389; A61B 2017/00274; A61B 2017/00367; A61B 17/0482; A61B 2017/0046; A61B 2017/0417; A61B 2017/0419; A61B 2090/08021; A61B 2090/0811; A61B 90/08
See application file for complete search history.

(56) References Cited

U.S. PATENT DOCUMENTS

| | | |
|---|---|---|
| 789,467 A | 5/1905 | West |
| 2,360,164 A | 10/1944 | Frank |
| 2,485,531 A | 10/1949 | William et al. |
| 2,579,192 A | 12/1951 | Alexander |
| 2,646,298 A | 7/1953 | Leary |
| 2,697,624 A | 12/1954 | Thomas et al. |
| 2,734,299 A | 2/1956 | Masson |
| 2,825,592 A | 3/1958 | Mckenzie |
| 3,326,586 A | 6/1967 | Frost et al. |
| 3,470,834 A | 10/1969 | Bone |
| 3,521,918 A | 7/1970 | Hammond |
| 3,541,591 A | 11/1970 | Hoegerman |
| 3,664,345 A | 5/1972 | Dabbs et al. |
| 3,713,680 A | 1/1973 | Pagano |
| 3,716,058 A | 2/1973 | Tanner |
| 3,756,638 A | 9/1973 | Stockberger |
| 3,873,140 A | 3/1975 | Bloch |
| 3,875,648 A | 4/1975 | Bone |
| 3,886,933 A | 6/1975 | Mori et al. |
| 3,931,667 A | 1/1976 | Merser et al. |
| 3,976,079 A | 8/1976 | Samuels et al. |
| 4,006,747 A | 2/1977 | Kronenthal et al. |
| 4,137,920 A | 2/1979 | Bonnet |
| 4,164,225 A | 8/1979 | Johnson et al. |
| 4,210,148 A | 7/1980 | Stivala |
| 4,235,238 A | 11/1980 | Ogiu et al. |
| 4,291,698 A | 9/1981 | Fuchs et al. |
| 4,409,974 A | 10/1983 | Freedland |
| 4,419,094 A | 12/1983 | Patel |
| 4,493,323 A | 1/1985 | Albright et al. |
| 4,513,746 A | 4/1985 | Aranyi et al. |
| 4,621,640 A | 11/1986 | Mulhollan et al. |
| 4,655,771 A | 4/1987 | Wallsten |
| 4,657,461 A | 4/1987 | Smith |
| 4,669,473 A | 6/1987 | Richards et al. |
| 4,705,040 A | 11/1987 | Mueller et al. |
| 4,714,281 A | 12/1987 | Peck |
| 4,738,255 A | 4/1988 | Goble et al. |
| 4,741,330 A | 5/1988 | Hayhurst |
| 4,744,364 A | 5/1988 | Kensey |
| 4,750,492 A | 6/1988 | Jacobs |
| 4,762,128 A | 8/1988 | Rosenbluth |
| 4,823,794 A | 4/1989 | Pierce |
| 4,863,439 A | 9/1989 | Sanderson |
| 4,899,743 A | 2/1990 | Nicholson et al. |
| 4,926,860 A | 5/1990 | Stice et al. |
| 4,946,468 A | 8/1990 | Li |
| 4,955,913 A | 9/1990 | Robinson |
| 4,968,315 A | 11/1990 | Gatturna |
| 5,002,550 A | 3/1991 | Li |
| 5,019,032 A | 5/1991 | Robertson |
| 5,041,129 A | 8/1991 | Hayhurst et al. |
| 5,046,513 A | 9/1991 | Gatturna et al. |
| 5,053,046 A | 10/1991 | Janese |
| 5,078,731 A | 1/1992 | Hayhurst |
| 5,080,660 A | 1/1992 | Buelna |
| 5,098,374 A | 3/1992 | Othel-Jacobsen et al. |
| 5,100,421 A | 3/1992 | Christoudias |
| 5,123,914 A | 6/1992 | Cope |
| 5,127,393 A | 7/1992 | McFarlin et al. |
| 5,129,912 A | 7/1992 | Noda et al. |
| 5,133,713 A | 7/1992 | Huang et al. |
| 5,159,925 A | 11/1992 | Neuwirth et al. |
| 5,160,339 A | 11/1992 | Chen et al. |
| 5,192,303 A | 3/1993 | Gatturna et al. |
| 5,203,787 A | 4/1993 | Noblitt et al. |
| 5,207,672 A | 5/1993 | Roth et al. |
| 5,217,470 A | 6/1993 | Weston |
| 5,217,486 A | 6/1993 | Rice et al. |
| 5,234,454 A | 8/1993 | Bangs |
| 5,236,445 A | 8/1993 | Hayhurst et al. |
| 5,237,984 A | 8/1993 | Williams et al. |
| 5,258,015 A | 11/1993 | Li et al. |
| 5,267,960 A | 12/1993 | Hayman et al. |
| 5,269,802 A | 12/1993 | Garber |
| 5,269,809 A | 12/1993 | Hayhurst et al. |
| 5,300,099 A | 4/1994 | Rudie |
| 5,322,501 A | 6/1994 | Mahmud-Durrani |
| 5,330,488 A | 7/1994 | Goldrath |
| 5,334,200 A | 8/1994 | Johnson |
| 5,336,240 A | 8/1994 | Metzler et al. |
| 5,354,271 A | 10/1994 | Voda |
| 5,358,511 A | 10/1994 | Gatturna et al. |
| 5,364,408 A | 11/1994 | Gordon |
| 5,366,490 A | 11/1994 | Edwards et al. |
| 5,368,599 A | 11/1994 | Hirsch et al. |
| 5,370,646 A | 12/1994 | Reese et al. |
| 5,380,334 A | 1/1995 | Torrie et al. |
| 5,391,182 A | 2/1995 | Chin |
| 5,403,348 A | 4/1995 | Bonutti |
| 5,405,352 A | 4/1995 | Weston |
| 5,411,520 A | 5/1995 | Nash et al. |
| 5,417,691 A | 5/1995 | Hayhurst |
| 5,435,805 A | 7/1995 | Edwards et al. |
| 5,470,337 A | 11/1995 | Moss |
| 5,472,446 A | 12/1995 | Torre |
| 5,478,003 A | 12/1995 | Green et al. |
| 5,480,406 A | 1/1996 | Nolan et al. |
| 5,499,994 A | 3/1996 | Tihon et al. |
| 5,501,690 A | 3/1996 | Measamer et al. |
| 5,507,754 A | 4/1996 | Green et al. |
| 5,522,846 A | 6/1996 | Bonutti |
| 5,531,763 A | 7/1996 | Mastri et al. |
| 5,536,240 A | 7/1996 | Edwards et al. |
| 5,540,655 A | 7/1996 | Edwards et al. |
| 5,540,704 A | 7/1996 | Gordon et al. |
| 5,545,171 A | 8/1996 | Sharkey et al. |
| 5,545,178 A | 8/1996 | Kensey et al. |
| 5,549,631 A | 8/1996 | Bonutti |
| 5,550,172 A | 8/1996 | Regula et al. |
| 5,554,162 A | 9/1996 | DeLange |
| 5,554,171 A | 9/1996 | Gatturna et al. |
| 5,562,689 A | 10/1996 | Green et al. |
| 5,569,305 A | 10/1996 | Bonutti |
| 5,571,104 A | 11/1996 | Li |
| 5,573,540 A | 11/1996 | Yoon |
| 5,578,044 A | 11/1996 | Gordon et al. |
| 5,591,177 A | 1/1997 | Lehrer |
| 5,593,421 A | 1/1997 | Bauer |
| 5,611,515 A | 3/1997 | Benderev et al. |
| 5,626,614 A | 5/1997 | Hart |
| 5,630,824 A | 5/1997 | Hart |
| 5,647,836 A | 7/1997 | Blake et al. |
| 5,653,717 A * | 8/1997 | Ko ................... A61B 17/0469 223/102 |
| 5,665,109 A | 9/1997 | Yoon |
| 5,667,486 A | 9/1997 | Mikulich et al. |
| 5,667,488 A | 9/1997 | Lundquist et al. |
| 5,669,917 A | 9/1997 | Sauer et al. |
| 5,690,649 A | 11/1997 | Li |
| 5,690,677 A | 11/1997 | Schmieding et al. |
| 5,697,950 A | 12/1997 | Fucci et al. |
| 5,707,394 A | 1/1998 | Miller et al. |

(56) References Cited

U.S. PATENT DOCUMENTS

| | | |
|---|---|---|
| 5,716,368 A | 2/1998 | Torre et al. |
| 5,718,717 A | 2/1998 | Bonutti |
| 5,725,556 A | 3/1998 | Moser et al. |
| 5,725,557 A | 3/1998 | Gatturna et al. |
| 5,733,306 A | 3/1998 | Bonutti |
| 5,741,276 A | 4/1998 | Poloyko et al. |
| 5,746,753 A | 5/1998 | Sullivan et al. |
| 5,749,846 A | 5/1998 | Edwards et al. |
| 5,749,889 A | 5/1998 | Bacich et al. |
| 5,752,963 A | 5/1998 | Allard et al. |
| 5,782,862 A | 7/1998 | Bonutti |
| 5,782,864 A | 7/1998 | Lizardi |
| 5,791,022 A | 8/1998 | Bohman |
| 5,800,445 A | 9/1998 | Ratcliff et al. |
| 5,807,403 A | 9/1998 | Beyar et al. |
| 5,810,848 A | 9/1998 | Hayhurst |
| 5,810,853 A | 9/1998 | Yoon |
| 5,814,072 A | 9/1998 | Bonutti |
| 5,830,179 A | 11/1998 | Mikus et al. |
| 5,830,221 A | 11/1998 | Stein et al. |
| 5,845,645 A | 12/1998 | Bonutti |
| 5,846,254 A | 12/1998 | Schulze et al. |
| 5,861,002 A | 1/1999 | Desai |
| 5,868,762 A | 2/1999 | Cragg et al. |
| 5,873,891 A | 2/1999 | Sohn |
| 5,879,357 A | 3/1999 | Heaton et al. |
| 5,897,574 A | 4/1999 | Bonutti |
| 5,899,911 A | 5/1999 | Carter |
| 5,899,921 A | 5/1999 | Caspari et al. |
| 5,904,679 A | 5/1999 | Clayman |
| 5,904,696 A | 5/1999 | Rosenman |
| 5,908,428 A | 6/1999 | Scirica et al. |
| 5,908,447 A | 6/1999 | Schroeppel et al. |
| 5,919,198 A | 7/1999 | Graves et al. |
| 5,919,202 A | 7/1999 | Yoon |
| 5,921,982 A | 7/1999 | Lesh et al. |
| 5,921,986 A | 7/1999 | Bonutti |
| 5,928,252 A | 7/1999 | Steadman et al. |
| 5,931,844 A | 8/1999 | Thompson et al. |
| 5,944,739 A | 8/1999 | Zlock et al. |
| 5,948,001 A | 9/1999 | Larsen |
| 5,948,002 A | 9/1999 | Bonutti |
| 5,954,057 A | 9/1999 | Li |
| 5,954,731 A | 9/1999 | Yoon |
| 5,954,747 A | 9/1999 | Clark |
| 5,964,732 A | 10/1999 | Willard |
| 5,971,447 A | 10/1999 | Steck |
| 5,971,967 A | 10/1999 | Willard |
| 6,010,514 A | 1/2000 | Burney et al. |
| 6,011,525 A | 1/2000 | Piole |
| 6,015,428 A | 1/2000 | Pagedas |
| 6,030,393 A | 2/2000 | Corlew |
| 6,033,413 A | 3/2000 | Mikus et al. |
| 6,033,430 A | 3/2000 | Bonutti |
| 6,036,701 A | 3/2000 | Rosenman |
| 6,048,351 A | 4/2000 | Gordon et al. |
| 6,053,908 A | 4/2000 | Crainich et al. |
| 6,056,722 A | 5/2000 | Jayaraman |
| 6,056,772 A | 5/2000 | Bonutti |
| 6,066,160 A | 5/2000 | Colvin et al. |
| 6,068,648 A | 5/2000 | Cole et al. |
| 6,080,167 A | 6/2000 | Fyell |
| 6,086,608 A | 7/2000 | Ek et al. |
| 6,110,183 A | 8/2000 | Cope |
| 6,117,133 A | 9/2000 | Zappala |
| 6,117,160 A | 9/2000 | Bonutti |
| 6,117,161 A | 9/2000 | Li et al. |
| 6,120,539 A | 9/2000 | Eldridge et al. |
| 6,132,438 A | 10/2000 | Fleischman et al. |
| 6,139,555 A | 10/2000 | Hart et al. |
| RE36,974 E | 11/2000 | Bonutti |
| 6,143,006 A | 11/2000 | Chan |
| 6,152,935 A | 11/2000 | Kammerer et al. |
| 6,156,013 A | 12/2000 | Mahurkar |
| 6,156,044 A | 12/2000 | Kammerer et al. |
| 6,159,207 A | 12/2000 | Yoon |
| 6,159,234 A | 12/2000 | Bonutti et al. |
| 6,200,329 B1 | 3/2001 | Fung et al. |
| 6,206,895 B1 | 3/2001 | Levinson |
| 6,206,907 B1 | 3/2001 | Marino et al. |
| 6,228,096 B1 | 5/2001 | Marchand |
| 6,258,124 B1 | 7/2001 | Darois et al. |
| 6,261,302 B1 | 7/2001 | Voegele et al. |
| 6,270,530 B1 | 8/2001 | Eldridge et al. |
| 6,280,460 B1 | 8/2001 | Bolduc et al. |
| 6,287,317 B1 | 9/2001 | Makower et al. |
| 6,290,711 B1 | 9/2001 | Caspari et al. |
| 6,306,158 B1 | 10/2001 | Bartlett |
| 6,312,448 B1 | 11/2001 | Bonutti |
| 6,319,263 B1 | 11/2001 | Levinson |
| 6,322,112 B1 | 11/2001 | Duncan |
| 6,332,889 B1 | 12/2001 | Sancoff et al. |
| 6,382,214 B1 | 5/2002 | Raz et al. |
| 6,398,795 B1 | 6/2002 | McAlister et al. |
| 6,423,079 B1 | 7/2002 | Blake, III |
| 6,425,900 B1 | 7/2002 | Knodel et al. |
| 6,425,919 B1 | 7/2002 | Lambrecht |
| 6,428,562 B2 | 8/2002 | Bonutti |
| 6,436,107 B1 | 8/2002 | Wang et al. |
| 6,461,355 B2 | 10/2002 | Svejkovsky et al. |
| 6,482,235 B1 | 11/2002 | Lambrecht et al. |
| 6,488,691 B1 | 12/2002 | Carroll et al. |
| 6,491,707 B2 | 12/2002 | Makower et al. |
| 6,494,888 B1 | 12/2002 | Laufer et al. |
| 6,500,184 B1 | 12/2002 | Chan et al. |
| 6,500,195 B2 | 12/2002 | Bonutti |
| 6,506,190 B1 | 1/2003 | Walshe |
| 6,506,196 B1 | 1/2003 | Laufer |
| 6,517,569 B2 | 2/2003 | Mikus et al. |
| 6,527,702 B2 | 3/2003 | Whalen et al. |
| 6,527,794 B1 | 3/2003 | McDevitt et al. |
| 6,530,932 B1 | 3/2003 | Swayze et al. |
| 6,533,796 B1 | 3/2003 | Sauer et al. |
| 6,544,230 B1 | 4/2003 | Flaherty et al. |
| 6,547,725 B1 | 4/2003 | Paolitto et al. |
| 6,551,328 B2 | 4/2003 | Kortenbach |
| 6,551,333 B2 | 4/2003 | Kuhns et al. |
| 6,565,578 B1 | 5/2003 | Peifer et al. |
| 6,569,187 B1 | 5/2003 | Bonutti et al. |
| 6,572,626 B1 | 6/2003 | Knodel et al. |
| 6,572,635 B1 | 6/2003 | Bonutti |
| 6,572,653 B1 | 6/2003 | Simonson |
| 6,582,453 B1 | 6/2003 | Tran et al. |
| 6,592,609 B1 | 7/2003 | Bonutti |
| 6,596,013 B2 | 7/2003 | Yang et al. |
| 6,599,311 B1 | 7/2003 | Biggs et al. |
| 6,626,913 B1 | 9/2003 | McKinnon et al. |
| 6,626,916 B1 | 9/2003 | Yeung et al. |
| 6,626,919 B1 | 9/2003 | Swanstrom |
| 6,629,534 B1 | 10/2003 | Goar et al. |
| 6,641,524 B2 | 11/2003 | Kovac |
| 6,641,592 B1 | 11/2003 | Sauer et al. |
| 6,656,182 B1 | 12/2003 | Hayhurst |
| 6,660,008 B1 | 12/2003 | Foerster et al. |
| 6,660,023 B2 | 12/2003 | McDevitt et al. |
| 6,663,589 B1 | 12/2003 | Halevy |
| 6,663,633 B1 | 12/2003 | Pierson |
| 6,663,639 B1 | 12/2003 | Laufer et al. |
| 6,699,263 B2 | 3/2004 | Cope |
| 6,702,846 B2 | 3/2004 | Mikus et al. |
| 6,706,047 B2 | 3/2004 | Trout et al. |
| 6,709,493 B2 | 3/2004 | DeGuiseppi et al. |
| 6,715,804 B2 | 4/2004 | Beers |
| 6,719,709 B2 | 4/2004 | Whalen et al. |
| 6,730,112 B2 | 5/2004 | Levinson |
| 6,736,823 B2 | 5/2004 | Darois et al. |
| 6,736,854 B2 | 5/2004 | Vadurro et al. |
| 6,740,098 B2 | 5/2004 | Abrams et al. |
| 6,767,037 B2 | 7/2004 | Wenstrom |
| 6,770,076 B2 | 8/2004 | Foerster |
| 6,773,438 B1 | 8/2004 | Knodel et al. |
| 6,773,441 B1 | 8/2004 | Laufer et al. |
| 6,790,213 B2 | 9/2004 | Cherok et al. |
| 6,802,846 B2 | 10/2004 | Hauschild et al. |

(56) References Cited

U.S. PATENT DOCUMENTS

| | | |
|---|---|---|
| 6,821,282 B2 | 11/2004 | Perry et al. |
| 6,821,285 B2 | 11/2004 | Laufer et al. |
| 6,821,291 B2 | 11/2004 | Bolea et al. |
| 6,835,200 B2 | 12/2004 | Laufer et al. |
| 6,905,475 B2 | 6/2005 | Hauschild et al. |
| 6,908,473 B2 | 6/2005 | Skiba et al. |
| 6,921,361 B2 | 7/2005 | Suzuki et al. |
| 6,926,732 B2 | 8/2005 | Derus et al. |
| 6,951,565 B2 | 10/2005 | Keane et al. |
| 6,986,775 B2 | 1/2006 | Morales et al. |
| 6,986,784 B1 | 1/2006 | Neiser et al. |
| 6,991,596 B2 | 1/2006 | Whalen et al. |
| 6,991,647 B2 | 1/2006 | Jadhav |
| 6,997,940 B2 | 2/2006 | Bonutti |
| 7,001,327 B2 | 2/2006 | Whalen et al. |
| 7,008,381 B2 | 3/2006 | Janssens |
| 7,011,688 B2 | 3/2006 | Gryska et al. |
| 7,015,253 B2 | 3/2006 | Escandon et al. |
| 7,041,111 B2 | 5/2006 | Chu |
| 7,048,698 B2 | 5/2006 | Whalen et al. |
| 7,048,747 B2 | 5/2006 | Arcia et al. |
| 7,060,077 B2 | 6/2006 | Gordon et al. |
| 7,063,715 B2 | 6/2006 | Onuki et al. |
| 7,081,126 B2 | 7/2006 | McDevitt et al. |
| 7,083,638 B2 | 8/2006 | Foerster |
| 7,087,073 B2 | 8/2006 | Bonutti |
| 7,089,064 B2 | 8/2006 | Manker et al. |
| 7,090,690 B2 | 8/2006 | Foerster et al. |
| 7,093,601 B2 | 8/2006 | Manker et al. |
| 7,105,004 B2 | 9/2006 | DiCesare et al. |
| 7,108,655 B2 | 9/2006 | Whalen et al. |
| 7,141,038 B2 | 11/2006 | Whalen et al. |
| 7,153,314 B2 | 12/2006 | Laufer et al. |
| 7,179,225 B2 | 2/2007 | Shluzas et al. |
| 7,226,558 B2 | 6/2007 | Nieman et al. |
| 7,232,448 B2 | 6/2007 | Battles et al. |
| 7,255,675 B2 | 8/2007 | Gertner et al. |
| 7,288,063 B2 | 10/2007 | Petros et al. |
| 7,303,108 B2 | 12/2007 | Shelton |
| 7,320,701 B2 | 1/2008 | Haut et al. |
| 7,322,974 B2 | 1/2008 | Swoyer et al. |
| 7,326,221 B2 | 2/2008 | Sakamoto et al. |
| 7,334,822 B1 | 2/2008 | Hines |
| 7,340,300 B2 | 3/2008 | Christopherson et al. |
| 7,399,304 B2 | 7/2008 | Gambale et al. |
| 7,402,166 B2 | 7/2008 | Feigl |
| 7,416,554 B2 | 8/2008 | Lam et al. |
| 7,417,175 B2 | 8/2008 | Oda et al. |
| 7,463,934 B2 | 12/2008 | Tronnes et al. |
| 7,481,771 B2 | 1/2009 | Fonseca et al. |
| 7,553,317 B2 | 6/2009 | William et al. |
| 7,608,108 B2 | 10/2009 | Bhatnagar et al. |
| 7,645,286 B2 | 1/2010 | Catanese et al. |
| 7,658,311 B2 | 2/2010 | Boudreaux |
| 7,674,275 B2 | 3/2010 | Martin et al. |
| 7,695,494 B2 | 4/2010 | Foerster |
| 7,704,261 B2 | 4/2010 | Sakamoto et al. |
| 7,727,248 B2 | 6/2010 | Smith et al. |
| 7,736,374 B2 | 6/2010 | Vaughan et al. |
| 7,758,594 B2 | 7/2010 | Lamson et al. |
| 7,766,923 B2 | 8/2010 | Catanese et al. |
| 7,766,939 B2 | 8/2010 | Yeung et al. |
| 7,780,682 B2 | 8/2010 | Catanese et al. |
| 7,815,655 B2 | 10/2010 | Catanese et al. |
| 7,887,551 B2 | 2/2011 | Bojarski et al. |
| 7,896,891 B2 | 3/2011 | Catanese et al. |
| 7,905,889 B2 | 3/2011 | Catanese et al. |
| 7,909,836 B2 | 3/2011 | McLean et al. |
| 7,914,542 B2 | 3/2011 | Lamson et al. |
| 7,951,158 B2 | 5/2011 | Catanese et al. |
| 8,007,503 B2 | 8/2011 | Catanese et al. |
| 8,043,309 B2 | 10/2011 | Catanese et al. |
| 8,157,815 B2 | 4/2012 | Catanese et al. |
| 8,211,118 B2 | 7/2012 | Catanese et al. |
| 8,216,254 B2 | 7/2012 | McLean et al. |
| 8,333,776 B2 | 12/2012 | Cheng et al. |
| 8,343,187 B2 | 1/2013 | Lamson et al. |
| 8,394,110 B2 | 3/2013 | Catanese et al. |
| 8,394,113 B2 | 3/2013 | Wei et al. |
| 8,425,535 B2 | 4/2013 | McLean et al. |
| 8,454,655 B2 | 6/2013 | Yeung et al. |
| 8,491,606 B2 | 7/2013 | Tong et al. |
| 8,529,584 B2 | 9/2013 | Catanese et al. |
| 8,603,106 B2 | 12/2013 | Catanese et al. |
| 8,628,542 B2 | 1/2014 | Merrick et al. |
| 8,663,243 B2 | 3/2014 | Lamson et al. |
| 8,668,705 B2 | 3/2014 | Johnston et al. |
| 8,715,239 B2 | 5/2014 | Lamson et al. |
| 8,715,298 B2 | 5/2014 | Catanese et al. |
| 8,758,366 B2 | 6/2014 | McLean et al. |
| 8,900,252 B2 | 12/2014 | Lamson et al. |
| 8,936,609 B2 | 1/2015 | Catanese et al. |
| 8,939,996 B2 | 1/2015 | Cheng et al. |
| 9,320,511 B2 | 4/2016 | McLean et al. |
| 9,504,461 B2 | 11/2016 | Catanese et al. |
| 9,549,739 B2 | 1/2017 | Catanese et al. |
| 9,931,192 B2 | 4/2018 | McLean et al. |
| 10,105,132 B2 | 10/2018 | Lamson et al. |
| 10,299,780 B2 | 5/2019 | Catanese et al. |
| 10,349,932 B2 | 7/2019 | Catanese et al. |
| 10,568,651 B2 | 2/2020 | Kostrzewski et al. |
| 10,702,261 B2 | 7/2020 | Stiggelbout |
| 11,298,115 B2 | 4/2022 | Yarra et al. |
| 11,801,041 B2 | 10/2023 | Cutts et al. |
| 2001/0041916 A1 | 11/2001 | Bonutti |
| 2001/0044639 A1 | 11/2001 | Levinson |
| 2002/0095064 A1 | 7/2002 | Beyar |
| 2002/0095154 A1 | 7/2002 | Atkinson et al. |
| 2002/0107540 A1 | 8/2002 | Whalen et al. |
| 2002/0128684 A1 | 9/2002 | Foerster |
| 2002/0161382 A1 | 10/2002 | Neisz et al. |
| 2002/0183740 A1 | 12/2002 | Edwards et al. |
| 2002/0193809 A1 | 12/2002 | Meade et al. |
| 2003/0060819 A1 | 3/2003 | McGovern et al. |
| 2003/0109769 A1 | 6/2003 | Lowery et al. |
| 2003/0191497 A1 | 10/2003 | Cope |
| 2003/0199860 A1 | 10/2003 | Loeb et al. |
| 2003/0204195 A1 | 10/2003 | Keane et al. |
| 2003/0229263 A1 | 12/2003 | Connors et al. |
| 2003/0236535 A1 | 12/2003 | Onuki et al. |
| 2004/0030217 A1 | 2/2004 | Yeung et al. |
| 2004/0043052 A1 | 3/2004 | Hunter et al. |
| 2004/0078046 A1 | 4/2004 | Barzell et al. |
| 2004/0122456 A1 | 6/2004 | Saadat et al. |
| 2004/0122474 A1 | 6/2004 | Gellman et al. |
| 2004/0147958 A1 | 7/2004 | Lam et al. |
| 2004/0181235 A1 | 9/2004 | Daignault et al. |
| 2004/0193191 A1 | 9/2004 | Starksen et al. |
| 2004/0193194 A1 | 9/2004 | Laufer et al. |
| 2004/0194790 A1 | 10/2004 | Laufer et al. |
| 2004/0243178 A1 | 12/2004 | Haut et al. |
| 2004/0243179 A1 | 12/2004 | Foerster |
| 2004/0243180 A1 | 12/2004 | Donnelly et al. |
| 2004/0243227 A1 | 12/2004 | Starksen et al. |
| 2004/0260345 A1 | 12/2004 | Foerster |
| 2005/0010203 A1 | 1/2005 | Edwards et al. |
| 2005/0055087 A1 | 3/2005 | Starksen |
| 2005/0065550 A1 | 3/2005 | Starksen et al. |
| 2005/0107811 A1 | 5/2005 | Starksen et al. |
| 2005/0107812 A1 | 5/2005 | Starksen et al. |
| 2005/0154401 A1 | 7/2005 | Weldon et al. |
| 2005/0165272 A1 | 7/2005 | Okada et al. |
| 2005/0177181 A1 | 8/2005 | Kagan et al. |
| 2005/0203344 A1 | 9/2005 | Orban et al. |
| 2005/0203550 A1 | 9/2005 | Laufer et al. |
| 2005/0216040 A1 | 9/2005 | Gertner et al. |
| 2005/0216078 A1 | 9/2005 | Starksen et al. |
| 2005/0251157 A1 | 11/2005 | Saadat et al. |
| 2005/0251206 A1 | 11/2005 | Maahs et al. |
| 2005/0256530 A1 | 11/2005 | Petros |
| 2005/0267405 A1 | 12/2005 | Shah |
| 2005/0273138 A1 | 12/2005 | To et al. |
| 2006/0025750 A1 | 2/2006 | Starksen et al. |
| 2006/0025784 A1 | 2/2006 | Starksen et al. |

(56) References Cited

U.S. PATENT DOCUMENTS

| | | |
|---|---|---|
| 2006/0025789 A1 | 2/2006 | Laufer et al. |
| 2006/0025819 A1 | 2/2006 | Nobis et al. |
| 2006/0026750 A1 | 2/2006 | Ballance |
| 2006/0030884 A1 | 2/2006 | Yeung et al. |
| 2006/0058817 A1 | 3/2006 | Starksen et al. |
| 2006/0089646 A1 | 4/2006 | Bonutti |
| 2006/0167477 A1 | 7/2006 | Arcia et al. |
| 2006/0195008 A1 | 8/2006 | Whalen et al. |
| 2006/0199996 A1 | 9/2006 | Caraballo et al. |
| 2006/0241694 A1 | 10/2006 | Cerundolo |
| 2006/0265042 A1 | 11/2006 | Catanese et al. |
| 2006/0276481 A1 | 12/2006 | Evrard et al. |
| 2006/0276871 A1 | 12/2006 | Lamson et al. |
| 2006/0282081 A1 | 12/2006 | Fanton et al. |
| 2007/0049929 A1 | 3/2007 | Catanese et al. |
| 2007/0049970 A1 | 3/2007 | Belef et al. |
| 2007/0060931 A1 | 3/2007 | Hamilton et al. |
| 2007/0088362 A1 | 4/2007 | Bonutti et al. |
| 2007/0112385 A1 | 5/2007 | Conlon |
| 2007/0142846 A1 | 6/2007 | Catanese et al. |
| 2007/0173888 A1 | 7/2007 | Gertner et al. |
| 2007/0260259 A1 | 11/2007 | Fanton et al. |
| 2007/0270885 A1* | 11/2007 | Weinert ............. A61B 17/0469 606/139 |
| 2008/0009888 A1 | 1/2008 | Ewers et al. |
| 2008/0021445 A1 | 1/2008 | Elmouelhi et al. |
| 2008/0021485 A1 | 1/2008 | Catanese et al. |
| 2008/0033458 A1 | 2/2008 | McLean et al. |
| 2008/0033460 A1 | 2/2008 | Ziniti et al. |
| 2008/0033488 A1 | 2/2008 | Catanese et al. |
| 2008/0039833 A1 | 2/2008 | Catanese et al. |
| 2008/0039872 A1 | 2/2008 | Catanese et al. |
| 2008/0039874 A1 | 2/2008 | Catanese et al. |
| 2008/0039875 A1 | 2/2008 | Catanese et al. |
| 2008/0039893 A1 | 2/2008 | McLean et al. |
| 2008/0039894 A1 | 2/2008 | Catanese et al. |
| 2008/0045978 A1 | 2/2008 | Kuhns et al. |
| 2008/0051810 A1 | 2/2008 | To et al. |
| 2008/0058710 A1 | 3/2008 | Wilk |
| 2008/0065120 A1 | 3/2008 | Zannis et al. |
| 2008/0082113 A1 | 4/2008 | Bishop et al. |
| 2008/0086172 A1 | 4/2008 | Martin et al. |
| 2008/0091220 A1 | 4/2008 | Chu |
| 2008/0091237 A1 | 4/2008 | Schwartz et al. |
| 2008/0119874 A1 | 5/2008 | Merves |
| 2008/0154378 A1 | 6/2008 | Pelo |
| 2008/0161852 A1 | 7/2008 | Kaiser et al. |
| 2008/0195145 A1 | 8/2008 | Bonutti et al. |
| 2008/0208220 A1 | 8/2008 | Shiono et al. |
| 2008/0228202 A1 | 9/2008 | Cropper et al. |
| 2008/0262424 A1 | 10/2008 | Hooft |
| 2008/0269737 A1 | 10/2008 | Elmouelhi et al. |
| 2009/0012537 A1 | 1/2009 | Green |
| 2009/0018553 A1 | 1/2009 | McLean et al. |
| 2009/0060977 A1 | 3/2009 | Lamson et al. |
| 2009/0112234 A1 | 4/2009 | Crainich et al. |
| 2009/0112537 A1 | 4/2009 | Okumura |
| 2010/0010631 A1 | 1/2010 | Otte et al. |
| 2010/0023024 A1 | 1/2010 | Zeiner et al. |
| 2010/0030262 A1 | 2/2010 | Mclean et al. |
| 2010/0030263 A1 | 2/2010 | Cheng et al. |
| 2010/0063351 A1 | 3/2010 | Witzmann et al. |
| 2010/0063542 A1 | 3/2010 | Burg et al. |
| 2010/0114162 A1 | 5/2010 | Bojarski et al. |
| 2010/0191045 A1 | 7/2010 | Gobron et al. |
| 2010/0240951 A1 | 9/2010 | Catanese et al. |
| 2010/0256442 A1 | 10/2010 | Ogdahl et al. |
| 2010/0261950 A1 | 10/2010 | Lund et al. |
| 2010/0286106 A1 | 11/2010 | Gat et al. |
| 2010/0286679 A1 | 11/2010 | Hoey et al. |
| 2010/0286717 A1 | 11/2010 | Heinrich et al. |
| 2010/0298948 A1 | 11/2010 | Hoey et al. |
| 2011/0040312 A1 | 2/2011 | Lamson et al. |
| 2011/0046648 A1 | 2/2011 | Johnston et al. |
| 2011/0054493 A1* | 3/2011 | McLean ............. A61B 17/0401 606/139 |
| 2011/0060349 A1 | 3/2011 | Cheng et al. |
| 2011/0082471 A1 | 4/2011 | Holcomb et al. |
| 2011/0105841 A1 | 5/2011 | Kutikov et al. |
| 2011/0160747 A1 | 6/2011 | McLean et al. |
| 2011/0166564 A1 | 7/2011 | Merrick et al. |
| 2011/0172755 A1 | 7/2011 | Nelson et al. |
| 2011/0190758 A1 | 8/2011 | Lamson et al. |
| 2011/0218387 A1 | 9/2011 | Lamson et al. |
| 2011/0245828 A1 | 10/2011 | Baxter et al. |
| 2011/0276081 A1 | 11/2011 | Kilemnik |
| 2012/0041533 A1 | 2/2012 | Bertolino et al. |
| 2012/0041534 A1 | 2/2012 | Clerc et al. |
| 2012/0083836 A1 | 4/2012 | Shelton, IV et al. |
| 2012/0245600 A1 | 9/2012 | McLean et al. |
| 2012/0265006 A1 | 10/2012 | Makower et al. |
| 2013/0096582 A1 | 4/2013 | Cheng et al. |
| 2013/0211431 A1 | 8/2013 | Wei et al. |
| 2013/0253574 A1 | 9/2013 | Catanese et al. |
| 2013/0253662 A1 | 9/2013 | Lamson et al. |
| 2013/0261383 A1 | 10/2013 | Catanese et al. |
| 2013/0261665 A1 | 10/2013 | Yeung et al. |
| 2013/0267772 A1 | 10/2013 | Catanese et al. |
| 2013/0268001 A1 | 10/2013 | Catanese et al. |
| 2013/0274799 A1 | 10/2013 | Catanese et al. |
| 2013/0289342 A1 | 10/2013 | Tong et al. |
| 2013/0296639 A1 | 11/2013 | Lamson et al. |
| 2013/0296889 A1 | 11/2013 | Tong et al. |
| 2013/0296935 A1 | 11/2013 | McLean et al. |
| 2013/0325143 A1 | 12/2013 | Lamson et al. |
| 2014/0005473 A1 | 1/2014 | Catanese et al. |
| 2014/0005690 A1 | 1/2014 | Catanese et al. |
| 2014/0031835 A1 | 1/2014 | Viker et al. |
| 2014/0088587 A1 | 3/2014 | Merrick et al. |
| 2014/0180067 A1 | 6/2014 | Stigall et al. |
| 2014/0236230 A1 | 8/2014 | Johnston et al. |
| 2014/0275756 A1 | 9/2014 | Bender et al. |
| 2014/0296881 A1 | 10/2014 | Ranucci et al. |
| 2014/0330290 A1* | 11/2014 | Tong ................. A61B 17/0482 606/139 |
| 2015/0025652 A1 | 1/2015 | McLean et al. |
| 2015/0127050 A1 | 5/2015 | Lamson et al. |
| 2015/0351743 A1 | 12/2015 | Stiggelbout |
| 2016/0022265 A1 | 1/2016 | Kawaura et al. |
| 2016/0045297 A1 | 2/2016 | Siegel et al. |
| 2016/0095685 A1 | 4/2016 | Vemuri et al. |
| 2016/0228107 A1* | 8/2016 | Madsen ............. A61B 17/0469 |
| 2016/0374669 A1 | 12/2016 | Overmyer et al. |
| 2017/0000598 A1 | 1/2017 | Bachar |
| 2017/0035410 A1 | 2/2017 | Catanese et al. |
| 2017/0135830 A1 | 5/2017 | Harkin et al. |
| 2017/0156723 A1 | 6/2017 | Keating et al. |
| 2018/0103945 A1 | 4/2018 | Ciulla et al. |
| 2018/0318114 A1 | 11/2018 | Huang et al. |
| 2019/0125334 A1 | 5/2019 | Tong et al. |
| 2019/0298334 A1 | 10/2019 | Catanese et al. |
| 2020/0038213 A1 | 2/2020 | Bly et al. |
| 2020/0121442 A1 | 4/2020 | Askeland |
| 2020/0170638 A1* | 6/2020 | Roslin et al. ...... A61B 17/0057 |
| 2021/0145619 A1 | 5/2021 | Bly et al. |
| 2021/0161641 A1 | 6/2021 | Bachar |
| 2021/0161642 A1 | 6/2021 | Jen et al. |
| 2021/0307641 A1 | 10/2021 | Rumbles et al. |
| 2022/0000445 A1 | 1/2022 | Datta et al. |
| 2022/0031303 A1 | 2/2022 | Yarra et al. |
| 2022/0031357 A1 | 2/2022 | Cutts et al. |
| 2022/0031389 A1 | 2/2022 | Fischell et al. |
| 2022/0061834 A1 | 3/2022 | Chung et al. |
| 2022/0125499 A1 | 4/2022 | Hoey et al. |
| 2022/0133462 A1 | 5/2022 | Kilemnik |
| 2022/0142464 A1 | 5/2022 | Petroff et al. |
| 2022/0240925 A1 | 8/2022 | Epstein et al. |
| 2022/0249219 A1 | 8/2022 | Chung et al. |
| 2022/0265262 A1 | 8/2022 | Melsheimer |
| 2022/0273918 A1 | 9/2022 | Ghriallais et al. |
| 2022/0378577 A1 | 12/2022 | Anderson et al. |

(56) References Cited

U.S. PATENT DOCUMENTS

| | | | |
|---|---|---|---|
| 2022/0395363 | A1 | 12/2022 | Ghriallais et al. |
| 2023/0022482 | A1 | 1/2023 | Dhavale |
| 2023/0329685 | A1 | 10/2023 | Cutts et al. |

FOREIGN PATENT DOCUMENTS

| | | |
|---|---|---|
| CN | 102112064 B | 6/2014 |
| CN | 105852938 A | 8/2016 |
| CN | 109009285 A | 12/2018 |
| CN | 109675177 A | 4/2019 |
| CN | 211156119 U | 8/2020 |
| CN | 112891032 A | 6/2021 |
| CN | 216221843 U | 4/2022 |
| DE | 10159470 A1 | 6/2003 |
| DE | 102019101987 A1 | 7/2020 |
| EP | 0246836 B1 | 12/1991 |
| EP | 0464480 A1 | 1/1992 |
| EP | 0632999 A1 | 1/1995 |
| EP | 1016377 A2 | 7/2000 |
| EP | 1482841 A1 | 12/2004 |
| EP | 1082941 B1 | 3/2005 |
| EP | 1006909 B1 | 1/2007 |
| EP | 1852071 A2 | 11/2007 |
| EP | 1584295 B1 | 2/2008 |
| EP | 1884198 A2 | 2/2008 |
| EP | 1884199 A1 | 2/2008 |
| EP | 1887976 A2 | 2/2008 |
| EP | 1670361 B1 | 4/2008 |
| EP | 1962720 B1 | 9/2008 |
| EP | 1331886 B1 | 12/2008 |
| EP | 1482840 B1 | 12/2008 |
| EP | 2111167 A1 | 10/2009 |
| EP | 2164427 B1 | 3/2010 |
| EP | 1484023 B1 | 5/2011 |
| EP | 2339970 A2 | 7/2011 |
| EP | 2345373 A1 | 7/2011 |
| EP | 2345374 A1 | 7/2011 |
| EP | 2600781 A2 | 6/2013 |
| EP | 2658458 A2 | 11/2013 |
| EP | 2658477 A2 | 11/2013 |
| EP | 2049023 B1 | 12/2014 |
| EP | 2344048 B1 | 9/2016 |
| EP | 3989844 B1 | 9/2023 |
| FR | 2750031 A1 | 12/1997 |
| JP | 5836559 A | 3/1983 |
| JP | 1984500876 A | 5/1984 |
| JP | 09122134 | 5/1997 |
| JP | 2000140111 A | 5/2000 |
| JP | 2001137254 A | 5/2001 |
| JP | 2004344427 A | 12/2004 |
| JP | 2009106755 A | 5/2009 |
| JP | 2009521278 A | 6/2009 |
| JP | 2011529745 A | 12/2011 |
| JP | 2012143622 A | 8/2012 |
| JP | 2023502729 A | 1/2023 |
| KR | 101534820 B1 | 7/2015 |
| RU | 2062121 C1 | 6/1996 |
| RU | 2112571 C1 | 6/1998 |
| RU | 2128012 C1 | 3/1999 |
| RU | 2221501 C2 | 1/2004 |
| SU | 825094 A | 4/1981 |
| WO | 1983004285 A1 | 12/1983 |
| WO | 1987001270 A1 | 3/1987 |
| WO | 1991008708 A1 | 6/1991 |
| WO | 1992010142 A1 | 6/1992 |
| WO | 1993004727 A1 | 3/1993 |
| WO | 1993015664 A1 | 8/1993 |
| WO | 1995000818 A1 | 1/1995 |
| WO | 2000040159 A1 | 7/2000 |
| WO | 2001026588 A2 | 4/2001 |
| WO | 2001028432 A1 | 4/2001 |
| WO | 2001039671 A1 | 6/2001 |
| WO | 2001049195 A1 | 7/2001 |
| WO | 2001065997 A2 | 9/2001 |
| WO | 2001095818 A1 | 12/2001 |
| WO | 2002028289 A1 | 4/2002 |
| WO | 2002030335 A2 | 4/2002 |
| WO | 2002032321 A1 | 4/2002 |
| WO | 2003039334 A2 | 5/2003 |
| WO | 2003077772 A1 | 9/2003 |
| WO | 2004000159 A2 | 12/2003 |
| WO | 2004017845 A1 | 3/2004 |
| WO | 2004019787 A2 | 3/2004 |
| WO | 2004019788 A2 | 3/2004 |
| WO | 2004030569 A2 | 4/2004 |
| WO | 2004103189 A1 | 12/2004 |
| WO | 2005034738 A2 | 4/2005 |
| WO | 2005094447 A2 | 10/2005 |
| WO | 2006127431 A2 | 11/2006 |
| WO | 2007053516 A2 | 5/2007 |
| WO | 2007064906 A2 | 6/2007 |
| WO | 2007075981 A2 | 7/2007 |
| WO | 2008006084 A2 | 1/2008 |
| WO | 2008014191 A2 | 1/2008 |
| WO | 2008043044 A2 | 4/2008 |
| WO | 2008043917 A2 | 4/2008 |
| WO | 2008097942 A1 | 8/2008 |
| WO | 2009009617 A1 | 1/2009 |
| WO | 2009135005 A1 | 11/2009 |
| WO | 2010011832 A1 | 1/2010 |
| WO | 2010014821 A2 | 2/2010 |
| WO | 2010014825 A1 | 2/2010 |
| WO | 2012018446 A2 | 2/2012 |
| WO | 2012028843 A1 | 3/2012 |
| WO | 2012091952 A2 | 7/2012 |
| WO | 2012091954 A2 | 7/2012 |
| WO | 2012091955 A2 | 7/2012 |
| WO | 2012091956 A2 | 7/2012 |
| WO | 2021190092 A1 | 9/2021 |

OTHER PUBLICATIONS

PCT International Search Report mailed Nov. 11, 2021, in PCT/US2021/042902.
PCT Written Opinion mailed Nov. 11, 2021, in PCT/US2021/042902.
First Office Action mailed Nov. 19, 2021, in U.S. Appl. No. 17/384,014.
Prosecution document: Response to first Office Action filed Feb. 10, 2022, in U.S. Appl. No. 17/384,014.
Bacharova, O.A., et al. "The Effect of Rhodiolae rosea Extract on Incidence Rate of Superficial Bladder Carcinoma Relapses", Kozin 1995.
Berges, Richard, et al. "Alternative Minimalinvasive Therapien Beim Benignen Prostatasyndrom", Medizin, Jg. 104, Heft 37, Sep. 14, 2007.
Borzhievski, et al., "Tactics of the Surgical Treatment of Patients With Prostatic Adenoma and Acute Urinary Retention," Urologia Nefrol (Mosk), Jan.-Feb. 1987, (1):39-43.
Extended European Search Report mailed Jan. 20, 2020 in EP Patent Application No. 19199026.6.
Hartung, Rudolf, et al. "Instrumentelle Therapie der benignen Prostatahyperplasie", Medizin, Deutsches Arzteblatt 97, Heft 15, Apr. 14, 2000.
Hofner, Klaus, et al., "Operative Therapie des benignen Prostatasyndroms", Medizin, Dtsch Arztebl, 2007; 104(36):A 2424-9.
Hubmann, R. "Geschichte der transurethralen Prostataeingriffe", Geschichte der Medizin, Urologe [B], 2000, 40:152-160.
Jonas, U., et al., "Benigne Prostatahyperplasie", Der Urologe 2006—[Sonderheft] 45:134-144.
Kruck, S., et al., "Aktuelle Therapiemoglichkeiten des Benignen Prostata-Syndroms", J Urol Urogynakol, 2009; 16(1): 19-22.
Miyake, Osamu. "Medical Examination and Treatment for BPH," Pharma Med, vol. 22, No. 3, 2004, p. 97-103.
Reich, O., et al., "Benignes Prostatasyndrom (BPS)," Der Urologe A Issue vol. 45, No. 6, Jun. 2006, p. 769-782.
Schauer, P., et al. "New applications for endoscopy: the emerging field of endoluminal and transgastric bariatric surgery", Surgical Endoscopy, (Apr. 24, 2006), 10 pgs.

(56) References Cited

OTHER PUBLICATIONS

Sharp, Howard T., M.D., et al. "Instruments and Methods—The 4-S Modification of the Roeder Knot: How to Tie It", Obstetrics & Gynecology, p. 1004-1006, vol. 90, No. 6, Dec. 1997.
Takashi, Daito. "Low-Invasive Treatment for BPH", Medico vol. 34, No. 10, p. 366-369, 2000.
Teruhisa, Ohashi. "Urinary Dysfunction by Lower Urinary Tract Obstraction in Male", Pharma Medica, vol. 8, No. 8, p. 35-39, 1990.
Tomohiko, Koyanagi, et al., "Surgery View of 21st Century," Urological Surgery, vol. 84, No. 1, p. 47-53, 2001.
Trapeznikov, et al., "New Technologies in the Treatment of Benign Prostatic Hyperplasia", Urologia Nefrol (Mosk), Jul.-Aug. 1996, (4):41-47.
Yeung, Jeff. "Treating Urinary Stress Incontenance Without Incision with Endoscopic Suture Anchor & Approximating Device," Aleeva Medical, Inc., 2007.
Notice of Allowance mailed Mar. 27, 2023, in U.S. Appl. No. 17/384,034.
Partial European Search Report, invitation to pay additional search fees, and search opinion mailed Dec. 20, 2023, in European Patent Application No. 23194169.1.

\* cited by examiner

HANDLE AND CARTRIDGE SYSTEM FOR MEDICAL INTERVENTIONS

CROSS REFERENCE TO RELATED APPLICATIONS

This application claims priority to U.S. provisional patent application No. 63/060,442, entitled "HANDLE AND CARTRIDGE SYSTEM FOR MEDICAL INTERVENTIONS" and filed on Aug. 3, 2020, which is herein incorporated by reference in its entirety.

BACKGROUND OF THE INVENTION

The present invention relates generally to medical devices, and more particularly to medical device systems including a handle and replaceable cartridge. In such systems, mechanical energy in the handle is transferred into the cartridge to manipulate tissue or anatomical structures within the body of a human or animal subject for the purpose of treating diseases or disorders.

Benign Prostatic Hyperplasia (BPH) is one of the most common medical conditions that affect men, especially elderly men. It has been reported that, in the United States, more than half of all men have histopathologic evidence of BPH by age 60 and, by age 85, approximately 9 out of 10 men suffer from the condition. Moreover, the incidence and prevalence of BPH are expected to increase as the average age of the population in developed countries increases.

The prostate gland enlarges throughout a man's life. In some men, the prostatic capsule around the prostate gland may prevent the prostate gland from enlarging further. This causes the inner region of the prostate gland to squeeze the urethra. This pressure on the urethra increases resistance to urine flow through the region of the urethra enclosed by the prostate. Thus, the urinary bladder has to exert more pressure to force urine through the increased resistance of the urethra. Chronic over-exertion causes the muscular walls of the urinary bladder to remodel and become stiffer. This combination of increased urethral resistance to urine flow and stiffness and hypertrophy of urinary bladder walls leads to a variety of lower urinary tract symptoms (LUTS) that may severely reduce the patient's quality of life. These symptoms include weak or intermittent urine flow while urinating, straining when urinating, hesitation before urine flow starts, feeling that the bladder has not emptied completely even after urination, dribbling at the end of urination or leakage afterward, increased frequency of urination particularly at night, and an urgent need to urinate.

In addition to patients with BPH, LUTS may also be present in patients with prostate cancer, prostate infections, and chronic use of certain medications (e.g. ephedrine, pseudoephedrine, phenylpropanolamine, antihistamines such as diphenhydramine, chlorpheniramine etc.) that cause urinary retention especially in men with prostate enlargement.

Although BPH is rarely life threatening, it can lead to numerous clinical conditions including urinary retention, renal insufficiency, recurrent urinary tract infection, incontinence, hematuria, and bladder stones.

In developed countries, a large percentage of the patient population undergoes treatment for BPH symptoms. It has been estimated that by the age of 80 years, approximately 25% of the male population of the United States will have undergone some form of BPH treatment. At present, the available treatment options for BPH include watchful waiting, medications (phytotherapy and prescription medications), surgery, and minimally invasive procedures.

For patients who choose the watchful waiting option, no immediate treatment is provided to the patient, but the patient undergoes regular exams to monitor progression of the disease. This is usually done on patients that have minimal symptoms that are not especially bothersome.

Surgical procedures for treating BPH symptoms include Transurethal Resection of the Prostate (TURP), Transurethral Electrovaporization of the Prostate (TVP), Transurethral Incision of the Prostate (TUIP), Laser Prostatectomy and Open Prostatectomy.

Minimally invasive procedures for treating BPH symptoms include Transurethral Microwave Thermotherapy (TUMT), Transurethral Needle Ablation (TUNA), Interstitial Laser Coagulation (ILC), and Prostatic Stents.

Many current methods of treating BPH carry a high risk of adverse effects. These methods and devices either require general or spinal anesthesia or have potential adverse effects that dictate that the procedures be performed in a surgical operating room followed by a hospital stay for the patient. The methods of treating BPH that carry a lower risk of adverse effects are also associated with a lower reduction in the symptom score. While several of these procedures can be conducted with local analgesia in an office setting, the patient does not experience immediate relief and in fact often experiences worse symptoms for weeks after the procedure until the body begins to heal. Additionally, many device approaches require a urethral catheter placed in the bladder, in some cases for weeks. In some cases, catheterization is indicated because the therapy actually causes obstruction during a period of time post-operatively, and in other cases it is indicated because of post-operative bleeding and potentially occlusive clot formation. While drug therapies are easy to administer, the results are suboptimal, take significant time to take effect, and often entail undesired side effects.

New devices and methods have been developed for various procedures to lift, compress, support, reposition, ablate, or otherwise alter prostatic tissue in a discrete procedure or in combination with treating BPH. Such devices and methods are disclosed in U.S. Pat. Nos. 7,645,286; 7,758,594; 7,766,923; 7,905,889; 7,951,158; 8,007,503; 8,157,815; 8,216,254; 8,333,776; 8,343,187; 8,394,110; 8,425,535; 8,663,243; 8,715,239; 8,715,298; 8,900,252; 8,936,609; 8,939,996; 9,320,511; 9,549,739; 10,105,132; and 10,299,780 which are hereby incorporated by reference herein in their entireties.

There remains a need for mechanical designs and systems to reliably, repeatably, and efficiently transfer energy from the handle to the cartridge of such devices. The present disclosure addresses these needs.

BRIEF SUMMARY OF THE INVENTION

Aspects of the present invention are directed towards mechanical designs and configurations for transferring mechanical energy from a handle to a cartridge for manipulating tissues and anatomical or other structures within the body of a human or animal subject for the purpose of treating diseases or disorders.

In one aspect, a cartridge includes a slidable cutter block connected to a slidable pusher block via an extension spring, wherein the cutter block and the pusher block are configured to slide in a linear within a body of the cartridge. The cartridge also includes a pivotable implant actuator within the body of the cartridge and engaged with the pusher block such that the implant actuator prevents the pusher block from sliding when the implant actuator is in a first position. A spring is in an extended position exerting a force tending to draw the cutter block and the pusher block toward each other. The cartridge includes a knob that moves from an unlocked position to a locked position such that the locked position secures the cartridge to the handle. The cartridge includes a pusher safety tab on the knob configured to engage the implant actuator when the knob is in the unlocked position such that the implant actuator cannot pivot while so engaged. The pusher safety tab on the knob is configured to disengage the implant actuator when the knob is in the locked position and allow the implant actuator to pivot. The cartridge includes a cutter pawl within the body of the cartridge and between the cutter block and the pusher block. The cutter pawl has an engaged position with the cutter block such that the cutter pawl prevents the cutter block from sliding towards the pusher block and a disengaged position with the cutter block such that the cutter pawl allows the cutter block to slide towards the pusher block. The pusher block is configured to slide into contact with the cutter pawl and cause the cutter pawl to pivot out of engagement with the cutter block. The cartridge includes an indicator window on a cover of the body of the cartridge. The indicator window indicates the position of the cutter block. The indicator window is configured to provide access to slide the cutter block. The cartridge includes an access window on the knob that provides access to the cutter pawl to allow the cutter pawl to be moved from the engaged position to the disengaged position without the pusher block contacting the cutter pawl.

In another aspect, a cartridge includes a cartridge body coupled to a shaft assembly having a long axis with a distal portion of the shaft assembly having a lumen running through the distal portion. The lumen has a lumen radius of curvature defined by the curving of the lumen as it runs in a first direction parallel to the long axis to run in a second direction transverse to the long axis. A needle assembly is slidably disposed within the shaft assembly and the cartridge body and having a needle distal portion such that the needle distal portion is configured to exit the shaft assembly from an exit port at which the lumen terminates. The needle distal portion has a needle radius of curvature defined by the curving of the needle as it runs in a first direction parallel to the long axis to run in a second direction transverse to the long axis, where the lumen radius of curvature and the needle radius of curvature are different. The cartridge includes a cutout on the shaft assembly configured to allow at least part of the needle distal portion to flex through the cutout. The cartridge includes an additional cutout on the shaft assembly configured to allow at least part of the needle distal portion to flex through the additional cutout. The cartridge includes a distal lumen wall configured with a wall radius of curvature that is at a tangent to a desired exit trajectory of the needle distal portion.

A system that includes a handle and a cartridge has a cam wheel within the handle and coupled to a trigger assembly included in the handle. A wheel actuator is coupled to the cam wheel such that a feature on the cam wheel is configured to cause the wheel actuator to pivot in a first direction when the feature contacts the wheel actuator. The wheel actuator has a flexure that is engaged when the wheel actuator pivots in the first direction and causes the wheel actuator to pivot in a second direction opposite the first direction when the feature no longer contacts the wheel actuator. The system includes a slidable pusher block and an implant actuator each within the cartridge. The implant actuator is engaged with the pusher block to prevent the pusher block from sliding. The wheel actuator disengages the implant actuator from the pusher block when the wheel actuator pivots in the first direction.

A system that includes a handle and a cartridge has a trigger assembly included in the handle and a lock tab on the trigger assembly configured to enter a cartridge bay of the handle when the trigger is in a working position such that a cartridge cannot be secured within the cartridge bay when the lock tab is at least partially within the cartridge bay. The system includes a lock surface on the cartridge configured to be engaged by the lock tab such that the cartridge cannot be removed from the cartridge bay when the trigger is in the working position. The cartridge can be removed from the cartridge bay when the trigger is in an initial position.

The system delivers an implant formed of a distal anchor component, a suture portion, and a proximal anchor component. The system has a pusher block configured to push the proximal anchor component onto the suture portion and a cutter block configured to cut the suture portion.

Other features and advantages of embodiments of the present invention will become apparent from the following description, taken in conjunction with the accompanying drawings, which illustrate, by way of example, certain principles of the invention.

DETAILED DESCRIPTION OF THE INVENTION

Generally, embodiments of the system of the present disclosure include mechanical designs and configurations for transferring mechanical energy from a handle to a cartridge for manipulating tissues and anatomical or other structures within the body of a human or animal subject for the purpose of treating diseases or disorders. The handle and cartridge cooperate to deliver an implant, or anchor assembly, within tissue. The cartridge is configured to carry the components of an anchor assembly. Multiple cartridges may be used with a single handle such that, during a procedure on an individual subject, multiple anchor assemblies may be deployed within tissue using that single handle.

Figure 1:
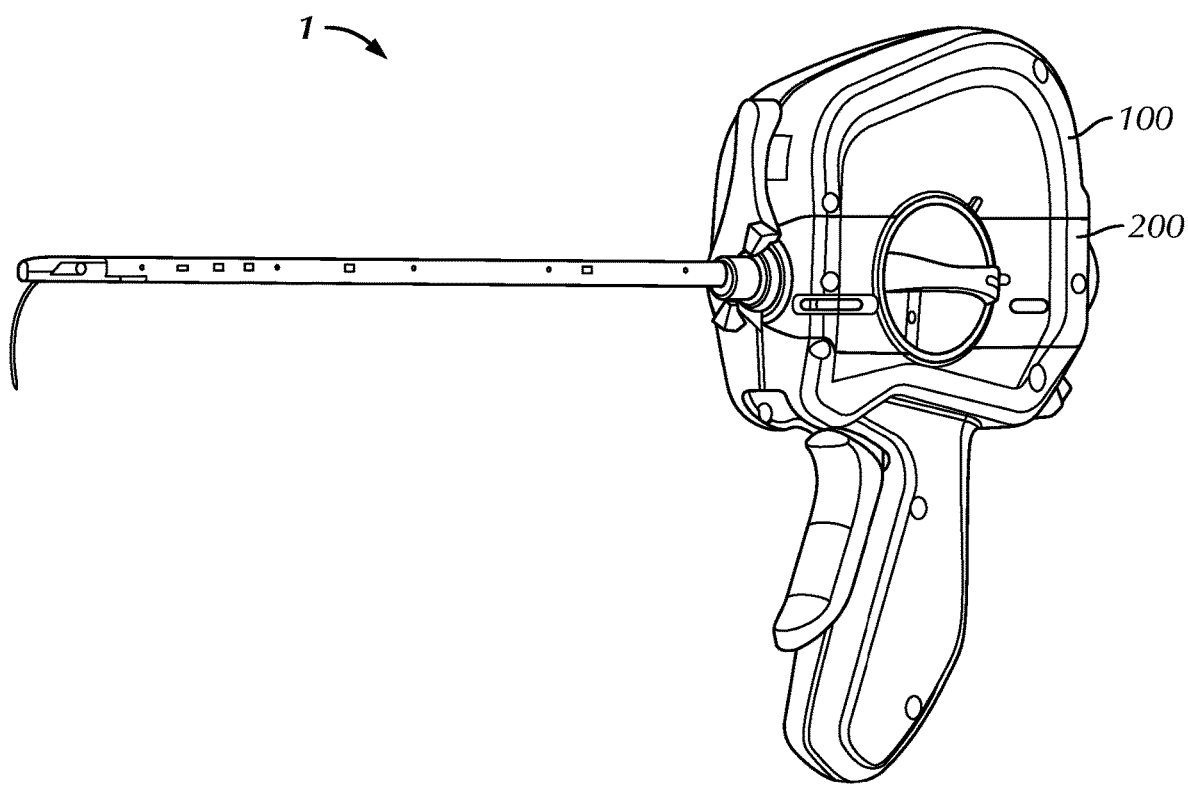
FIG. 1 is a perspective view of one embodiment of a system, including a handle and cartridge, for treating benign prostatic hyperplasia.

Turning now to the figures, which are provided by way of example and not limitation, FIG. 1 is a perspective view of one embodiment of a system 1, including a handle 100 and a cartridge 200, for treating benign prostatic hyperplasia. The handle 100 includes sources of mechanical energy that are transferred to the cartridge 200 to deploy the anchor assembly contained within the cartridge 200. The handle 100 is configured such that the energy can be restored to these mechanical energy sources while the first cartridge is being used and/or prior to the insertion of a second cartridge. The handle 100 is designed to reliably deliver energy to multiple cartridges in sequence before a new handle is required. The multiple uses of the handle 100 places unique constraints on the mechanical features of the handle 100 to facilitate the reliable, repeatable transfer of energy from the handle to the cartridge.

Figure 2A:
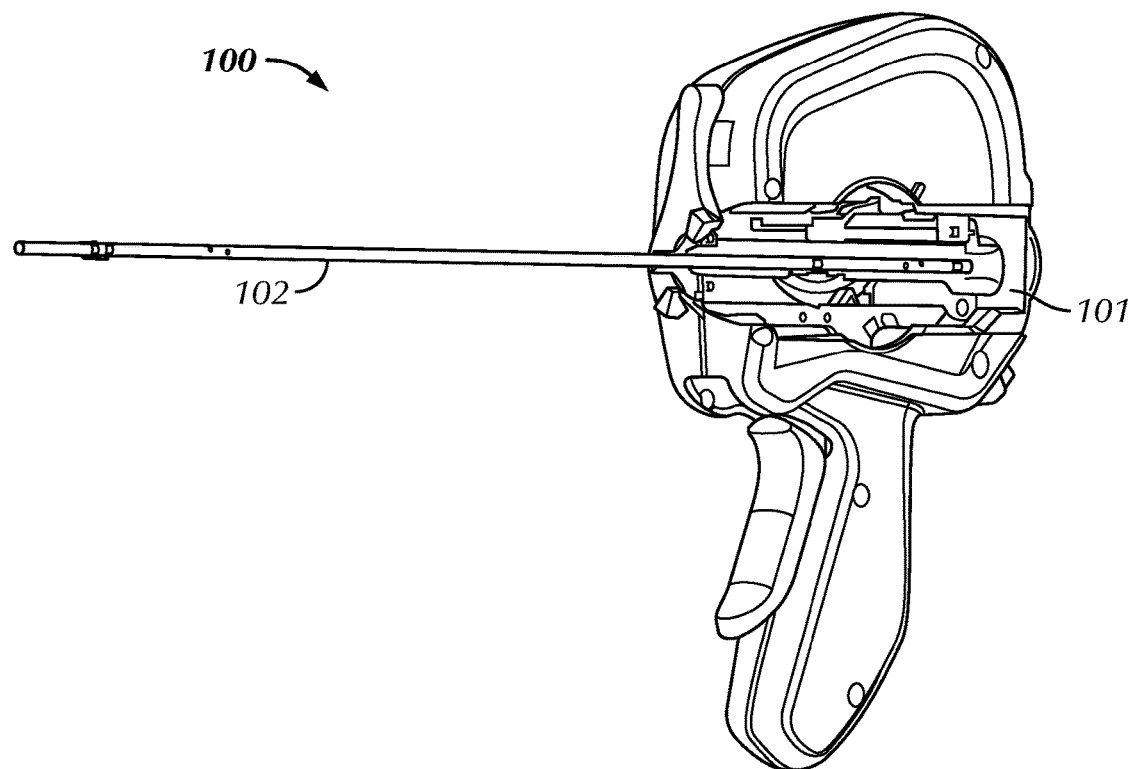
FIG. 2A is a perspective view of a handle of one embodiment of a system for treating benign prostatic hyperplasia in which the cartridge has been removed.
Figure 2B:
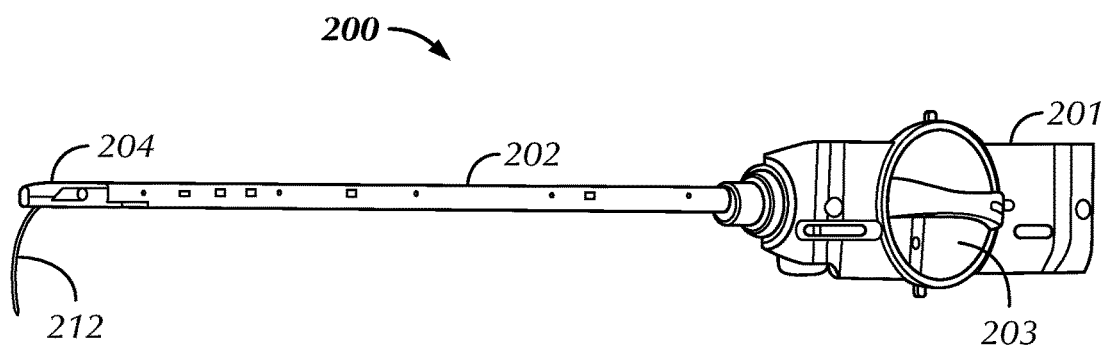
FIG. 2B is a perspective view of a cartridge removed from a handle of one embodiment of a system for treating benign prostatic hyperplasia.

FIG. 2A is a perspective view of a handle 100 and FIG. 2B is a perspective view of a cartridge 200 of one embodiment of a system for treating benign prostatic hyperplasia. FIGS. 2A and 2B show the handle 100 and the cartridge 200 disengaged from one another. The handle 100 includes a cartridge bay 101 into which the cartridge 200 can be securely inserted. The cartridge 200 includes a cartridge body 201 that can be positioned to securely engage the cartridge 200 in the cartridge bay 101 of the handle 100. The handle 100 includes a scope tube 102, which is configured to accommodate an endoscopic instrument within a lumen of the scope tube 102. The scope tube 102 facilitates visualization of a treatment site when the system is used to deploy anchor assemblies to tissue. The cartridge 200 includes a shaft assembly 202, which includes parts of other assemblies (such as a needle assembly 210, a suture assembly 220, and a cutter assembly 230 described in further detail herein). The scope tube 102 and the shaft assembly 202 are configured to couple together when the handle 100 and cartridge 200 are engaged with one another. Thus, the handle 100 and the cartridge 200 securely engage one another through the interaction of the cartridge bay 101 with the cartridge body 201 and the scope tube 102 with the shaft assembly 202. The cartridge knob 203 can be rotated from an unlocked position to a locked position to secure the coupling between the cartridge 200 and the handle 100.

FIG. 2B depicts a needle distal portion 212 extending from a shaft distal portion 204. The needle assembly 210 is configured to move between a fully retracted position, in which the entire needle assembly is within the shaft assembly 202 and cartridge body 201, to a fully extended position, in which the needle distal portion 212 extends from a shaft distal portion 204. The needle distal portion 212 contains components of the anchor assembly that is delivered to tissue.

Figure 3:
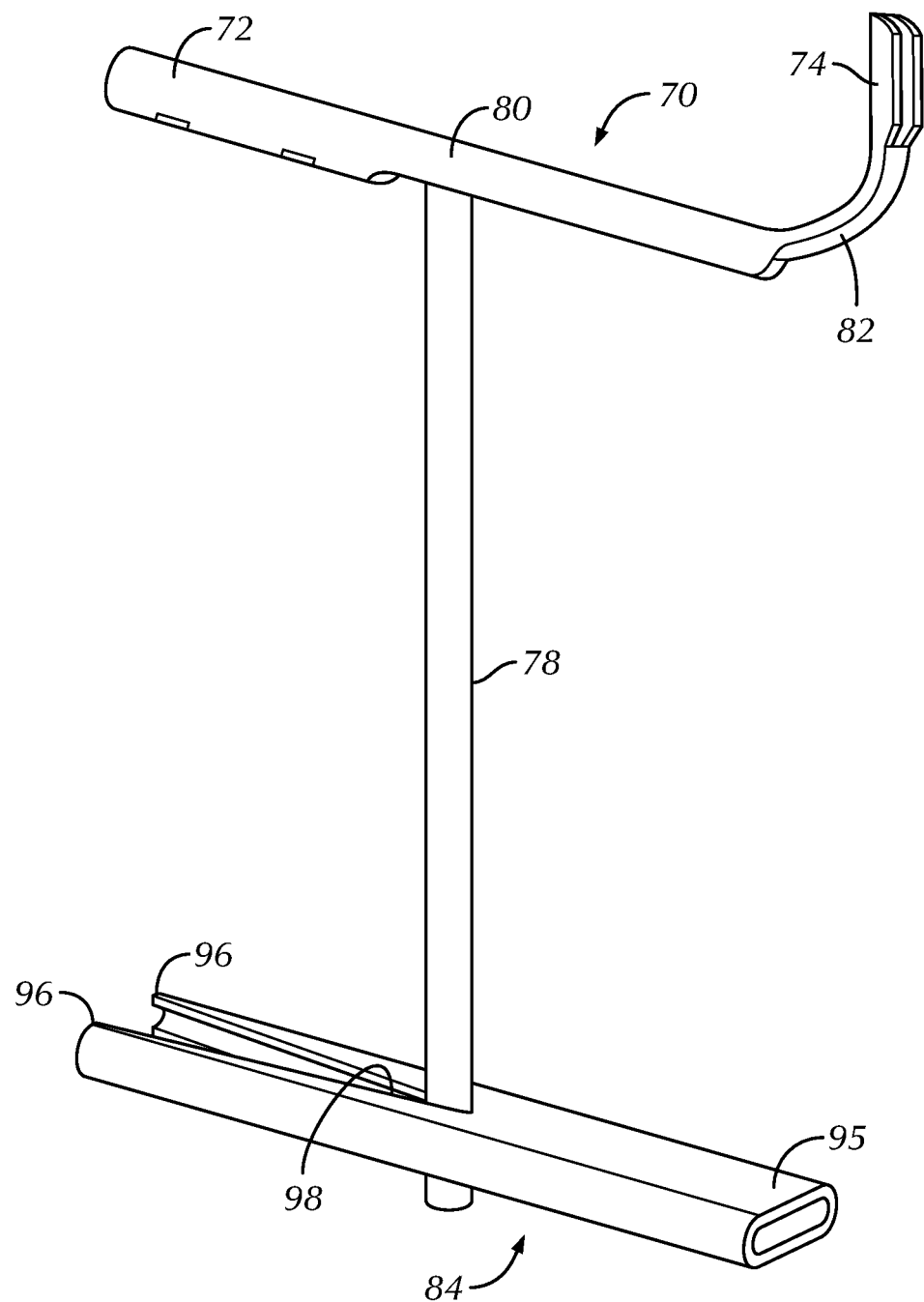
FIG. 3 is a perspective view of one embodiment of an anchor assembly.

FIG. 3 is a perspective view of one embodiment of an anchor assembly. In an unconstrained configuration, the distal anchor component 70 includes a head portion 72 which is generally orthogonally oriented with respect to a tail portion 74. While housed in the needle distal portion 212 and prior to deployment at a target area, the distal anchor component 70 is constrained to a generally straight configuration, only subsequently assuming the unconstrained (i.e., orthogonally oriented) configuration upon deployment from the needle assembly 210.

In certain embodiments, the distal anchor component 70 is formed from a nitinol base stock that is generally tubular and can be shape-set to include the orthogonally oriented configuration of the head portion 72 with respect to the tail portion 74. A suture 78 is attached to the distal anchor component 70. In one embodiment, a polyethylene terephthalate (PET) suture portion 78 is thermoformed onto locking features in the distal anchor component 70. The distal anchor component 70 may be locally heated to re-flow the suture onto the end of the distal anchor component 70 and into cutouts on the distal anchor component 70. The distal anchor component 70 may be attached to the suture portion 78 through any of several known techniques for bonding a PET material to a nitinol material.

In one embodiment, a mid-section 80 of the distal anchor component 70 provides a structural transition from the head portion 72 to the tail portion 74 and has a portion of a side wall removed in the area of mid-section 80. A further portion of the side wall is removed to define a connector section 82 of the tail portion 74 which extends from the mid-section 80. In one embodiment, this connector section 82 includes a bend that creates the orthogonally oriented configuration. Thus, in its pre-implanted form, the anchor assembly can include a distal anchor component 70 whose initial engagement with a suture portion 78 is generally coaxial.

Still referring to FIG. 3, in one embodiment the proximal anchor component 84 includes prongs 96 that grip the suture portion 78. The interior structure of the prongs 96 functions to disrupt the surface of the suture portion 78, both pressing into the suture portion 78 and compressing the suture portion 78 between the prongs 96. A tab 98 can extend from one or more of the prongs 96 to help create secure engagement between the proximal anchor component 84 and the suture portion 78.

In certain embodiments, the proximal anchor component 84 is present in the shaft assembly 202 in a configuration that is separate and disconnected from the distal anchor component 70 and the suture portion 78, which are engaged with each other and contained within the needle assembly 210. After the distal anchor component 70 and the suture portion 78 have been placed within tissue, the proximal anchor component 84 is securely engaged with the suture portion 78 to form the fully assembled anchor assembly. To facilitate engagement of the proximal anchor component 84 with the suture portion 78, the proximal anchor component 84 includes a rigid, generally cylindrical back end 95. This a rigid, generally cylindrical back end 95 can be used to push the proximal anchor component 84 into engagement with the suture 78 via transfer of the mechanical energy in the handle 100.

Figure 4A:
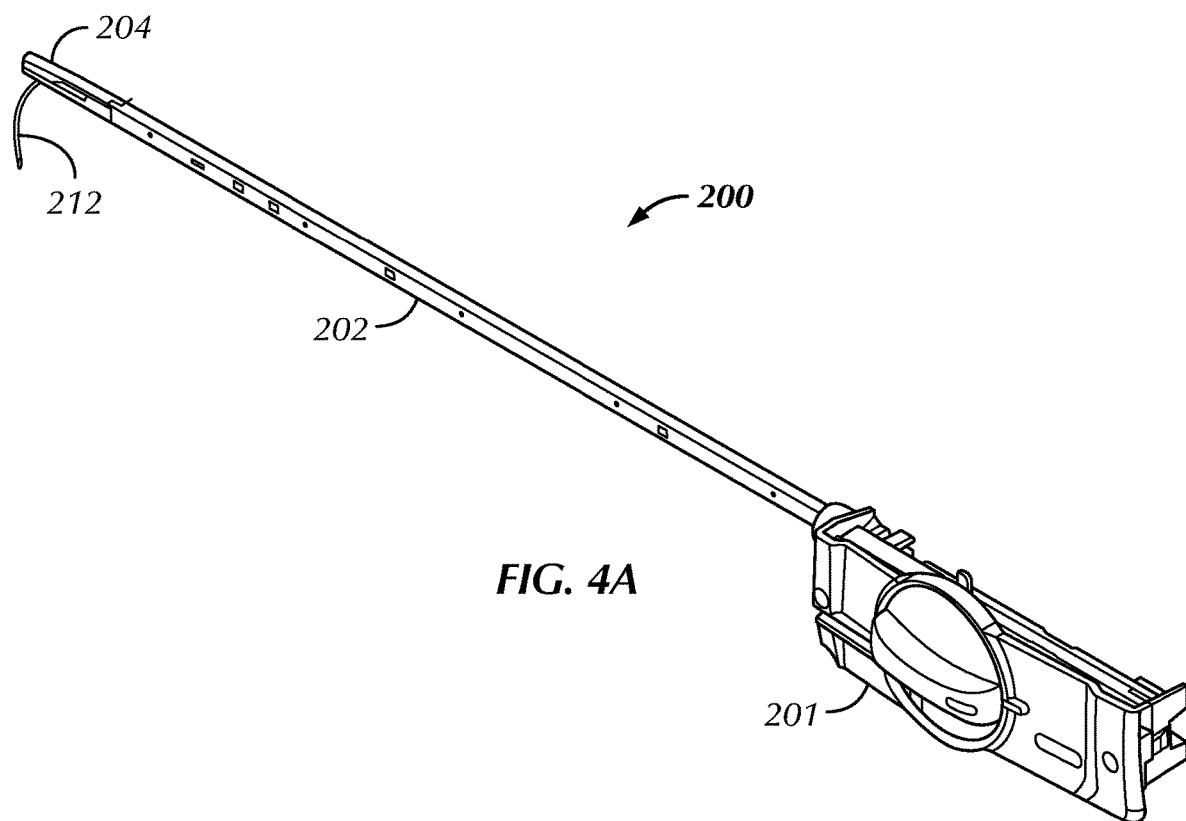
FIG. 4A is an isometric view of a cartridge of one embodiment of a system for treating benign prostatic hyperplasia.
Figure 4B:
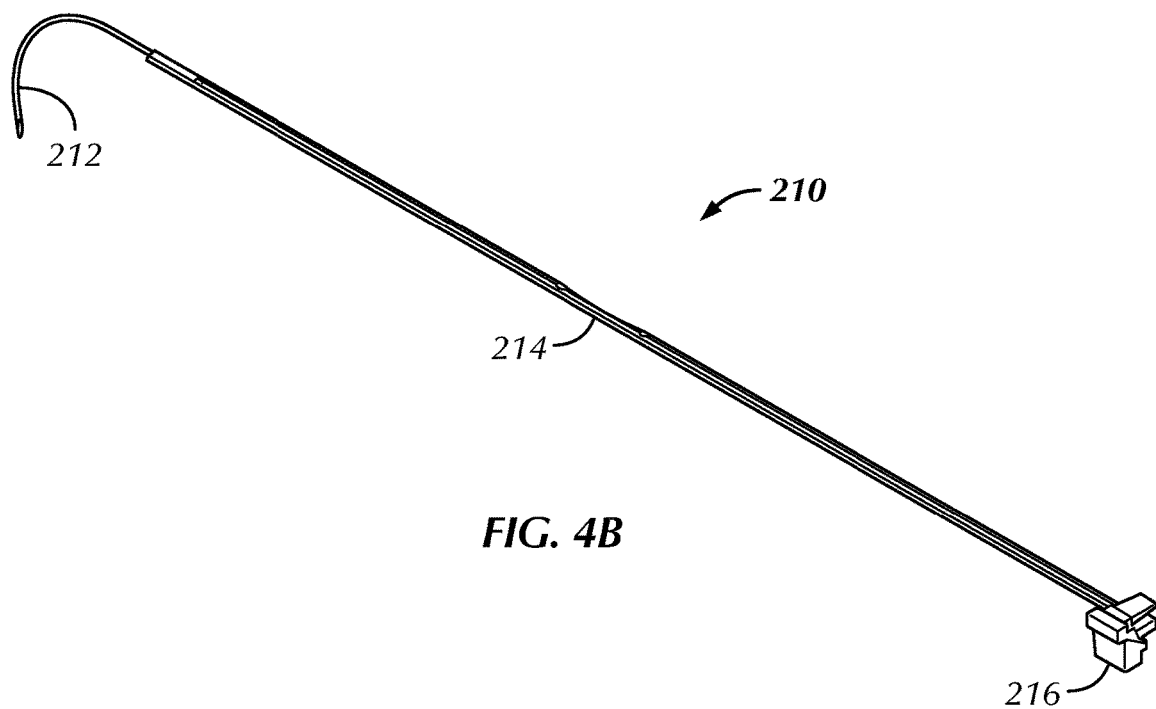
FIG. 4B is an isometric view of a needle assembly that is contained within a cartridge of one embodiment of a system for treating benign prostatic hyperplasia.

FIG. 4A is an isometric view of a cartridge 200 of one embodiment of a system for treating benign prostatic hyperplasia and FIG. 4B is an isometric view of a needle assembly 210 that is contained within such a cartridge 200. The needle assembly 210 includes a needle distal portion 210, a needle shaft 212, and a needle proximal portion 216. In one embodiment, the needle distal portion 210 is formed from nitinol and shape-set into a curved configuration in an unconstrained state. The needle assembly 210 is configured to slide along the long axis of the shaft assembly 202 of the cartridge 200. The needle assembly 210 is initially in a fully retracted position, in which the entire needle assembly is within the shaft assembly 202 and the cartridge body 201. When the needle assembly 210 is slid distally along the long axis of the shaft assembly 202 from its initial position, the needle distal portion 212 extends from a shaft distal portion 204 and eventually reaches a fully extended position. The needle assembly 210 can be slid proximally to retract the needle distal portion 212 back to its position within the shaft assembly 202. A significant part of the proximal length of the needle distal portion 212 is capable of assuming a substantially straight configuration when the needle distal portion 212 is within the shaft assembly 202. As described in further detail herein, the needle proximal portion 216 interacts with the mechanisms in the handle to transmit energy from the handle to the needle assembly 210 to deploy and retract the needle distal portion 212.

In certain embodiments, there can be noticeable amounts of friction between the needle assembly 210 and the shaft assembly 202 when the needle assembly 210 slides with respect to the shaft assembly 202. In some cases, the friction between the needle assembly 210 and the shaft assembly 202 can interfere with the ability of the needle distal portion 212 to move through the shaft distal portion 204. In some cases, such friction can slow the velocity of the needle distal portion 212 as it exits the shaft distal portion 204 and thereby compromise the effective treatment of a patient. That is, in the case of treating benign prostatic hyperplasia, the needle distal portion 212 should move into tissue with sufficient velocity such that the distal tip of the needle distal portion 212 can penetrate through the tough tissue capsule that surrounds the prostate gland.

There are various sources for the friction between the needle assembly 210 and the shaft assembly 202 when the needle assembly 210 slides with respect to the shaft assembly 202. For example, discontinuities or imperfections along the inner surfaces of the shaft assembly 202 and/or the outer surface of the needle assembly 210 can increase friction between the needle assembly 210 and the shaft assembly 202. One important source of friction is the restraining force exerted on the needle distal portion 212 to induce it to be substantially straight along a significant part of its proximal length. That is, the shape-set configuration of the needle distal portion 212 includes a pre-determined radius of curvature that the needle distal portion 212 assumes when in an unconstrained state. This pre-determined radius of curvature is designed so that the needle distal portion 212 penetrates tissue at a particular angle (or range of angles) and at a particular position (or range of positions) with respect to the distal exit point of the needle distal portion 212 from the shaft distal portion 204. The method of treating benign prostatic hyperplasia performed by embodiments of the system described herein relies on a generally transverse path of the needle through tissue with respect to the long axis of the shaft assembly 202.

The pre-determined radius of curvature enables the needle distal portion 212 to penetrate tissue along such a generally transverse path. However, as described herein, a significant part of the proximal length of the needle distal portion 212 is constrained to be substantially straight when the needle distal portion 212 is within the shaft distal portion 204. While the needle distal portion 212 is comparatively flexible, constraining the needle distal portion 212 does create multiple points of contact along the inner surface of the shaft assembly 202 and the inner surface of the shaft distal portion 204.

Figure 5A:
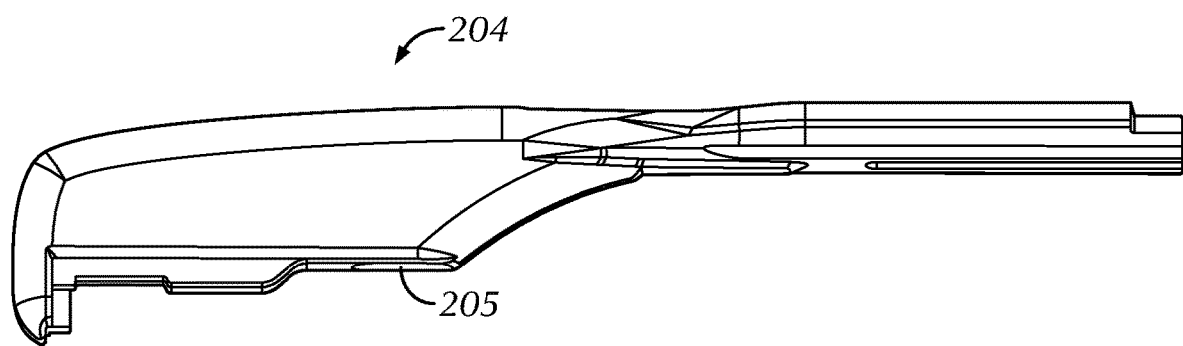
FIG. 5A is a side view of a portion of a distal tip component of a cartridge of one embodiment of a system for treating benign prostatic hyperplasia.
Figure 5B:
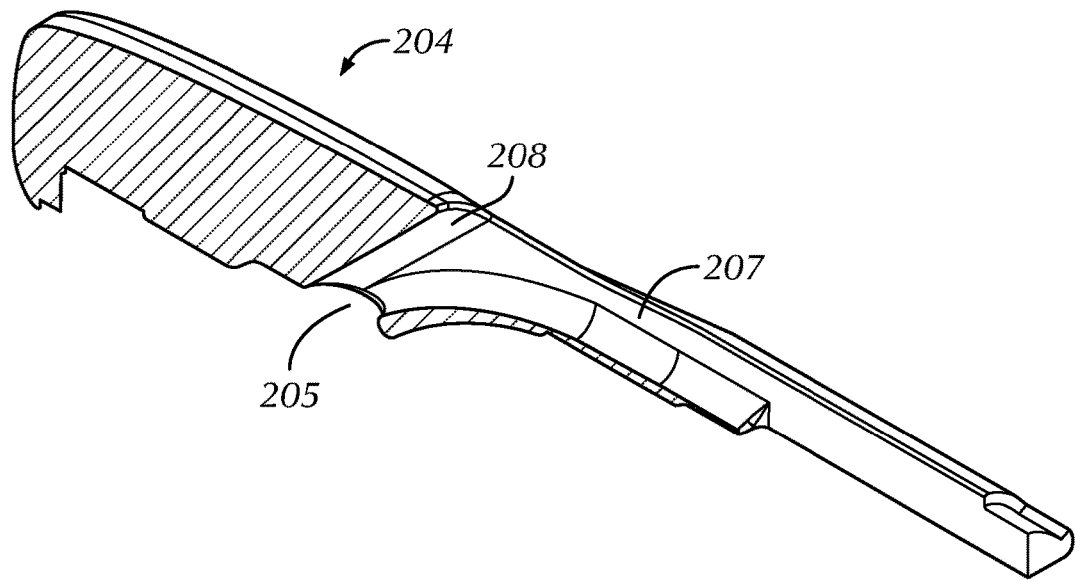
FIG. 5B is an isometric, cross-sectioned view of a distal tip component of a cartridge of one embodiment of a system for treating benign prostatic hyperplasia.

FIG. 5A is a side view of a portion of a distal tip component of a cartridge of one embodiment of a system for treating benign prostatic hyperplasia and FIG. 5B is an isometric, cross-sectioned view of the distal tip component. The shaft distal portion 204 includes a shaft distal portion exit port 205 from which the needle distal portion (not pictured) emerges when the needle distal portion is extended from the shaft distal portion 204. The shaft distal portion exit port 205 is the distal terminus of a shaft distal portion lumen 207. The shaft distal portion lumen 207 has a certain effective radius of curvature as the lumen transitions from running along the long axis of the shaft assembly to running in a direction transverse to the long axis of the shaft assembly. An aspect of that transition is the shaft distal portion interior exit wall 208, which is essentially the distal-most portion of the shaft distal portion lumen 207. Thus, when the needle assembly is present within the shaft assembly, the effective radius of curvature of the shaft distal portion lumen 207 and the shaft distal portion interior exit wall 208 can strongly influence the amount of friction that the needle assembly experiences when slid with respect to the shaft assembly.

Figure 6A:
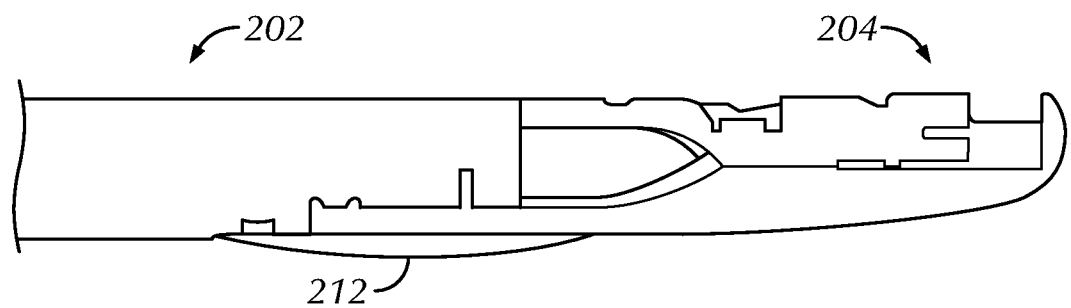
FIG. 6A is a side view of a portion of the distal end of a handle and cartridge of one embodiment of a system for treating benign prostatic hyperplasia.
Figure 6B:
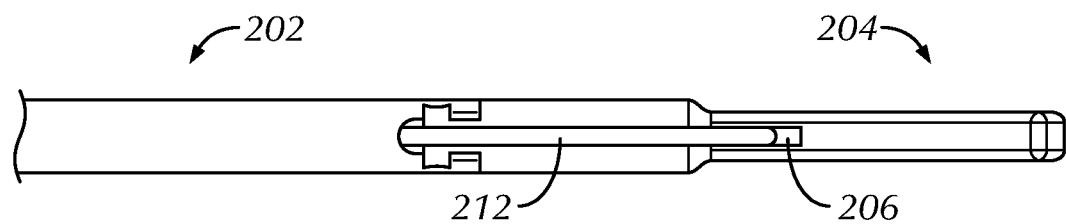
FIG. 6B is a bottom view of a portion of the distal end of a handle and cartridge of one embodiment of a system for treating benign prostatic hyperplasia.

FIG. 6A is a side view and FIG. 6B is a bottom view of a portion of the distal end of a handle and cartridge of one embodiment of a system for treating benign prostatic hyperplasia. FIGS. 6A and 6B depict the needle assembly in a retracted position within the shaft assembly 202 and shaft distal portion 204. That is, the needle assembly is being constrained to be substantially straight as compared to its shape-set configuration, which has a radius of curvature that positions the distal tip of the needle in a direction transverse to the long axis of the needle assembly. However, a shaft distal portion cutout 206 provides an opening between the interior and exterior of the shaft distal portion 204 and a portion of the needle distal portion 212 protrudes through the shaft distal portion cutout 206. The shaft distal portion cutout 206 allows at least part of the needle distal portion 212 to flex through a part of the bottom surface of the shaft distal portion 204, which allows the needle distal portion 212 to assume a smaller radius of curvature than would be possible if there were no shaft distal portion cutout 206. That is, the shaft distal portion cutout 206 allows for there to be less constraining force on the needle distal portion 212. The needle distal portion 212 does not contact a hard surface in the interior of the shaft distal portion 204 and this reduces the number of surfaces that the needle distal portion 212 contacts while moving with respect to the shaft distal portion 204. Fewer surface contacts can mean less overall friction during movement. Further, the shaft distal portion cutout 206 can help maintain the preferred exit trajectory of the needle distal portion 212 by accommodating part of the shape-set radius of curvature. In some embodiments, cutouts may be present along other parts of the shaft assembly 202. These cutouts can also reduce the number of surfaces that the needle assembly contacts while moving with respect to the shaft assembly 202.

Figure 7A:
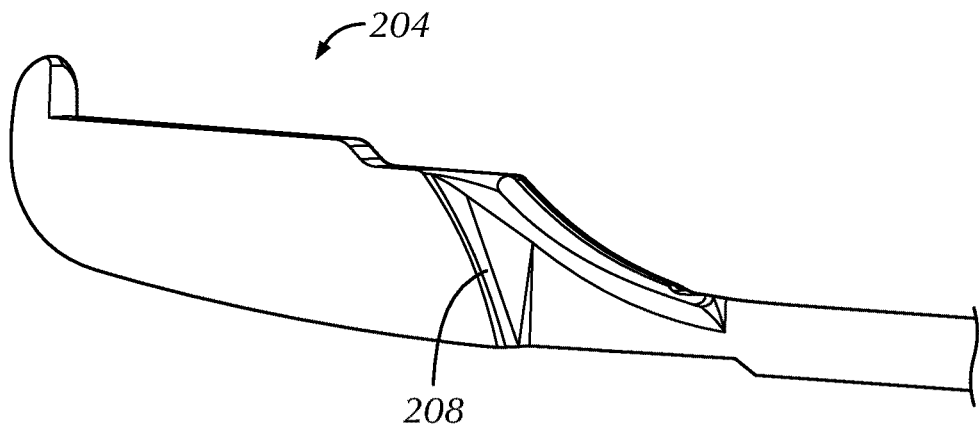
FIG. 7A is a perspective, sectional view of a distal portion of a cartridge of another embodiment of a system for treating benign prostatic hyperplasia.
Figure 7B:
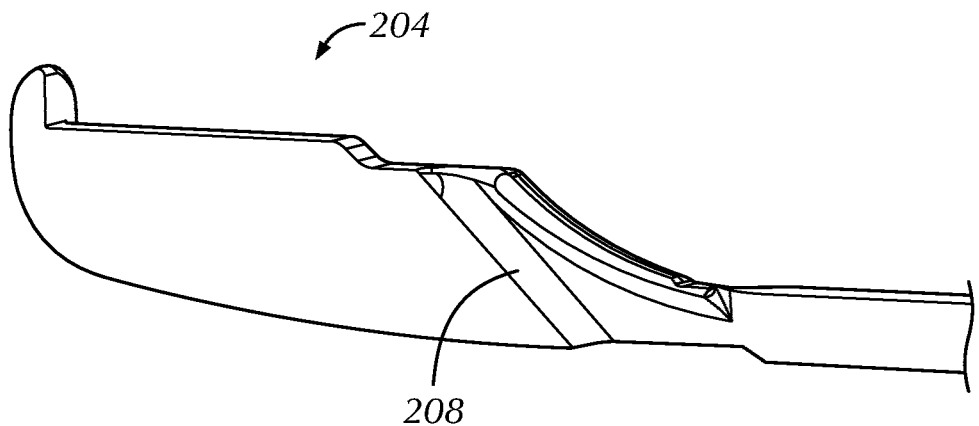
FIG. 7B is a perspective, sectional view of a distal portion of a cartridge of another embodiment of a system for treating benign prostatic hyperplasia.
Figure 7C:
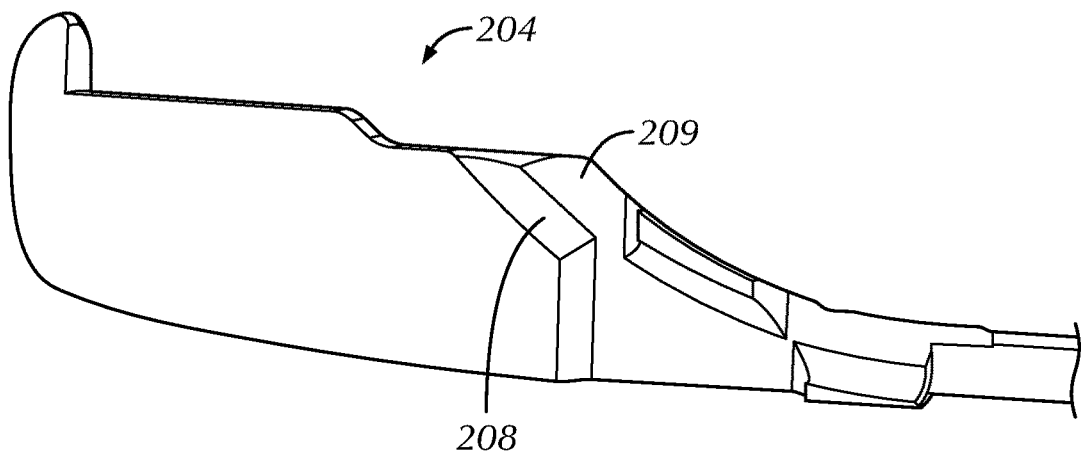
FIG. 7C is a perspective, sectional view of a distal portion of a cartridge of another embodiment of a system for treating benign prostatic hyperplasia.

FIGS. 7A, 7B, and 7C are perspective, sectional views of distal portions of cartridges of various embodiments of a system for treating benign prostatic hyperplasia. These embodiments illustrate various arrangements of the shaft distal portion interior exit wall 208. These embodiments intend to reduce the contact points and/or friction experienced by the needle assembly as it slides with respect to the shaft assembly. In FIG. 7A, the shaft distal portion interior exit wall 208 is configured with a radius of curvature that is at a tangent to the desired exit trajectory of the needle. In FIG. 7B, the shaft distal portion interior exit wall 208 is configured with a straight section where the entire section is angled at a tangent to the desired exit trajectory of the needle. In FIG. 7C, the shaft distal portion interior exit wall 208 is configured with a partial exit wall and a shaft distal portion upper cutout 209 on the upper surface. The shaft distal portion upper cutout 209 is intended to reduce the number of contact points between the shaft distal portion lumen and the needle assembly. Further, the shaft distal portion interior exit wall 208 is formed to minimize the presence of surface discontinuities, such as flash, burrs, or sharp edges.

Figure 8:
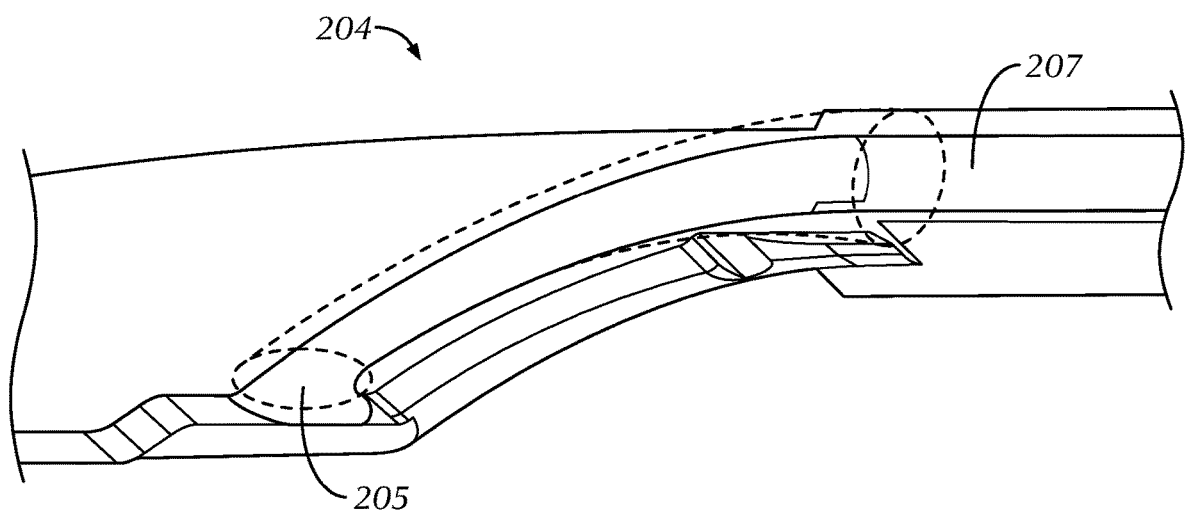
FIG. 8 is a perspective, cutaway view of a distal portion of a cartridge of one embodiment of a system for treating benign prostatic hyperplasia.

FIG. 8 is a perspective, cutaway view of a distal portion of a cartridge of one embodiment of a system for treating benign prostatic hyperplasia. FIG. 8 illustrates one embodiment of the configuration of the shaft distal portion lumen 207 as the lumen curves towards the shaft distal portion exit port 205. In this configuration, the curved section of the shaft distal portion lumen 207 includes a tapered cross-sectional dimension such that the cross-sectional area of the shaft distal portion lumen 207 is larger at the proximal end of the curved section than at the distal end of the curved section. In one embodiment, the cross-sectional area and the cross-sectional shape of the shaft distal portion exit port 205 is incrementally larger than the outer diameter of the needle proximal portion. In one embodiment, the curvature of the curved section of the shaft distal portion lumen 207 matches the desired exit trajectory of the needle proximal portion.

Figure 9:
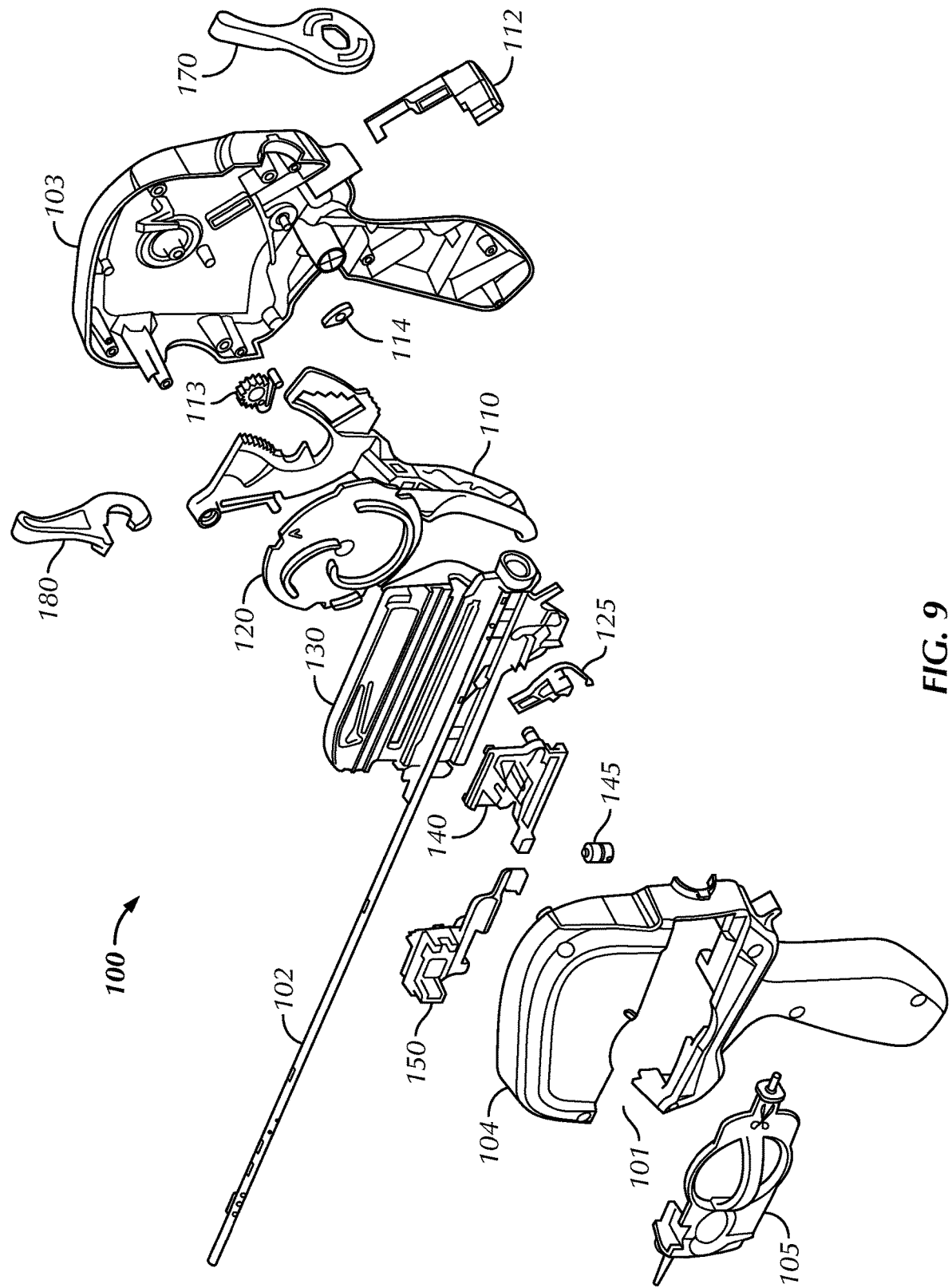
FIG. 9 is an exploded, isometric view of a handle of a system for treating benign prostatic hyperplasia.

FIG. 9 is an exploded, isometric view of one embodiment of a handle of a system for treating benign prostatic hyperplasia. The handle 100 includes a right handle case 103, a left handle case 104, and a cartridge bay 101 formed in the left handle case 104. The handle 100 is designed to transmit the energy stored in several springs (not pictured) within the handle 100 to a cartridge to enable the treatment of a patient. The energy is transmitted via the interaction of various mechanisms within the handle 100. A removable scope seal 105 covers the cartridge bay 101 and couples to the scope tube 102.

The mechanisms in the handle 100 include a handle trigger assembly 110, which is operatively connected to a handle trigger spring (not pictured) such that the handle trigger spring provides force sufficient to return the handle trigger assembly 110 to its initial position after the handle trigger assembly 110 has been squeezed and released by a user. A ratchet 114, which is connected to a ratchet spring (not pictured), affects the motion of the handle trigger assembly 110 such that the handle trigger assembly 110 does not return to its initial position prior to being moved (e.g. squeezed) to a predetermined position by a user. A safety 112 is connected to the handle trigger assembly 110 to ensure that the handle trigger assembly 110 is not operated accidentally. The handle trigger assembly 110 is connected to a drive gear 113, which is connected to a cam wheel 120.

The cam wheel 120 rotates about a central axis and, via structures and features on the cam wheel, triggers certain motions within the handle 100 as the cam wheel 120 rotates. There are multiple sleds operatively connected to the cam wheel 120, and the sleds move in a linear direction along a lateral axis of the handle 100. There are multiple springs that impart force to the multiple sleds to provide mechanical energy sufficient to deliver an implant. A cartridge includes multiple tab assemblies that mate with the sleds via slots in the sled such that the energy imparted by the operation of the mechanisms in the handle (such as the springs) is transmitted to the mechanisms in the cartridge.

A wheel actuator 125 is operatively connected to the cam wheel 120 and an implant sled 160, which is connected to an implant spring that provides energy related to the delivery of the implant. A needle sled 140 is operatively connected to the cam wheel 120 and an axle 145, and a needle sled spring provides energy related to the delivery of the implant. A suture sled 150 is operatively connected to the cam wheel 120, and a suture sled spring provides energy related to the delivery of the implant.

The handle 100 includes various other parts, such as a cover plate 130, a scope lock 170, a sheath lock 180, and various screws and/or fasteners to assemble the handle. The cover plate 130 provides the interior base for the cartridge bay 101. The scope tube 102, the scope lock 170, the scope seal 105, and the sheath lock 180 provide functionality for attaching an endoscope and other ancillary equipment (such as a surgical sheath) to facilitate the procedure.

Figure 10:
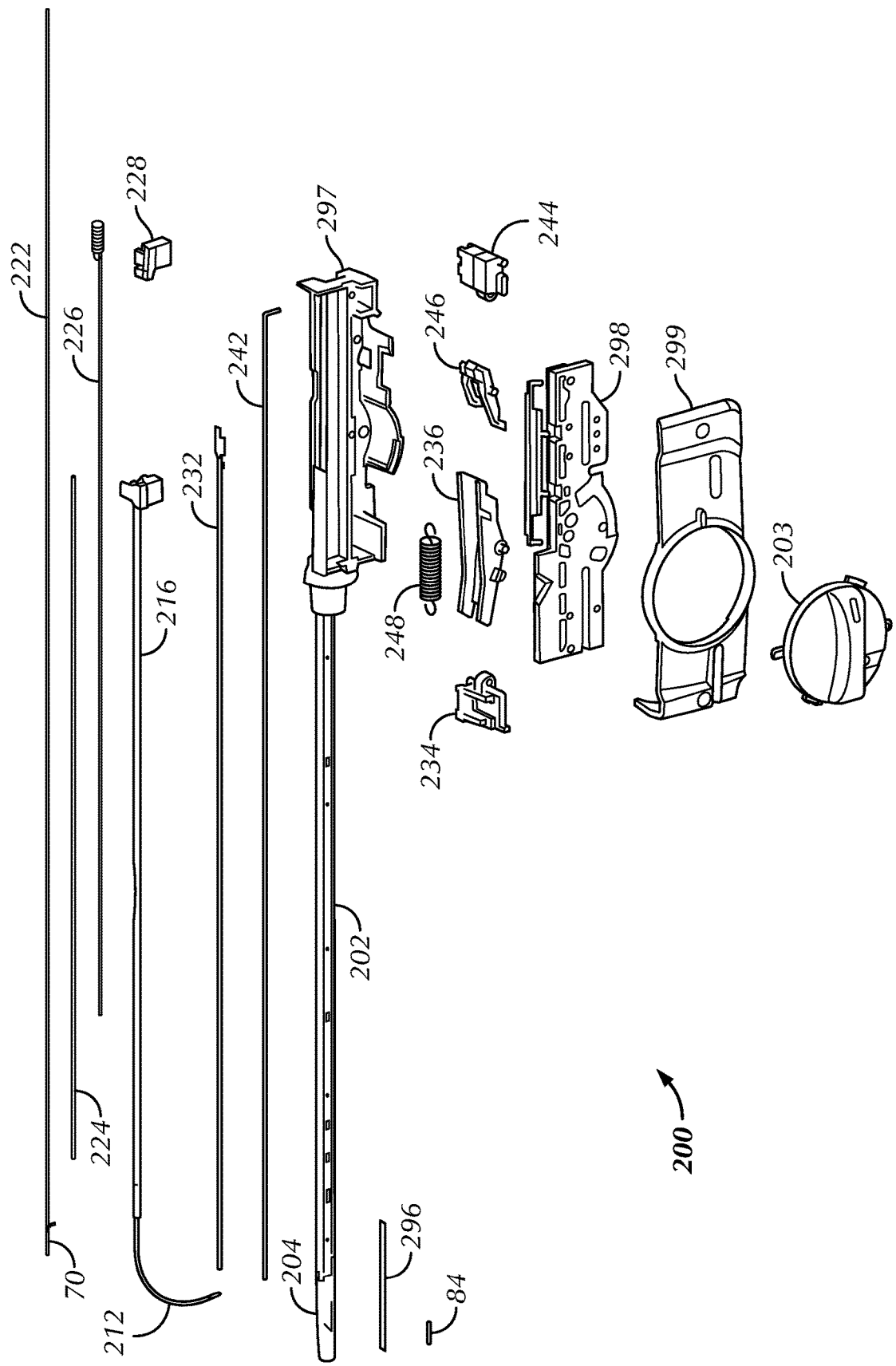
FIG. 10 is an exploded, isometric view of one embodiment of a cartridge of a system for treating benign prostatic hyperplasia.

FIG. 10 is an exploded, isometric view of one embodiment of a cartridge of a system for treating benign prostatic hyperplasia. In this embodiment, the cartridge 200 includes a cartridge cover 299 coupled to a cartridge base 298. These two parts couple with a shaft support 297 to form the cartridge body. The cartridge knob 203 couples to the cartridge cover 299.

The shaft support 297 is attached to the shaft assembly 202, which includes the shaft distal portion 204. An atraumatic tape 296 is present on a surface of the shaft distal portion 204 and helps reduce tissue trauma that could result from the tissue interacting with the various openings and joints on the shaft distal portion 204 (such as those described in FIGS. 5A and 5B). The proximal anchor component 84 is contained within the shaft distal portion 204 in a configuration that is separate and disconnected from the distal anchor component 70 and the suture portion (as described herein with respect to FIG. 3).

When the proximal anchor component 84 is connected to the distal anchor component 70 and the suture portion 78 as part of the implant deployment process, it is done via the action of the pusher assembly, which includes a pusher 242 connected with a pusher block 244. A cutter assembly, which cuts the suture 222 to create the suture portion 78 during the implant deployment process, includes a cutter 232 and a cutter block 234. The movement of the cutter assembly and the pusher assembly is coordinated by the interactions of the cutter pawl 236, the implant actuator 246, and the implant spring 248, as is described in more detail herein.

A suture assembly includes the suture 222, a suture support tube 224, a suture safety 226, and a suture proximal portion 228. The distal anchor component 70 is attached to a distal end portion of the suture 222 as described herein with respect to FIG. 3. The distal portion of the suture assembly and the distal anchor component 70 are contained within the needle assembly distal portion 212, which in turn is contained within the shaft assembly until the needle assembly distal portion 212 is moved into tissue during the implant deployment process. The movement of the needle assembly proximal portion 216 and the suture assembly proximal portion 228 is coordinated via the interaction of these features with mechanisms in the handle 100, as is described in more detail herein.

Referring again to the implant deployment process and to FIGS. 3, 4A, 4B, and 10, the anchor assembly (or implant) is deployed via a sequence of steps. The needle distal portion 212 extends from a shaft distal portion 204 to a fully extended position such that at least part of the needle distal portion 212 penetrates a tissue surface in a patient, such as the outer capsule of the prostate gland. The distal anchor component 70 and a distal portion of the suture 222 are contained within the needle distal portion 212 and move with the needle distal portion 212 to penetrate tissue.

Next, while the distal anchor component 70 and a distal portion of the suture 222 are held in place, the needle assembly 210 moves proximally such that the needle distal portion 212 moves to a partially retracted position. That is, the needle distal portion 212 moves proximally with respect to its fully extended position but is not yet completely retracted within the shaft assembly 202. The suture support tube 224 helps maintain the position of the distal anchor component 70 and a distal portion of the suture 222 while the needle assembly 210 moves proximally. Thus, the distal anchor component 70 and a distal portion of the suture 222 remain near the tissue surface and are no longer within the needle distal portion 212.

In a next step, the needle assembly 210 moves further proximally to be retracted within the shaft assembly 202 while the suture assembly also moves proximally. The tail portion 74 of the distal anchor component 70 is pulled snug against the tissue surface, which causes the distal anchor component 70 to pivot about the mid-section 80 such that the distal anchor component 70 is now transverse to a distal portion of the suture 222.

In a next step, the pusher assembly moves distally to push the proximal anchor component onto a distal portion of the suture 222 and this movement defines the suture portion 78 that becomes a component of the final anchor assembly implanted in the patient. And the cutter assembly moves proximally to pull a cutting edge through the suture. At this point, the anchor assembly is now completely detached from the cartridge and handle system.

The handle and cartridge system enables the multiple steps of deploying an anchor assembly through multiple squeezes of the handle trigger assembly by the user. That is, the relative motions of all the mechanisms in the handle and cartridge and the timing of those motions occurs via multiple squeezes of the handle trigger assembly. Referring now to FIG. 9, the handle trigger assembly 110 interacts with the cam wheel 120 via the drive gear 113 and the ratchet 114. The cam wheel 120 is the principal mechanism for the way in which the handle trigger assembly 110 drives the motion and timing of the various mechanisms in the handle and cartridge system.

Figure 11A:
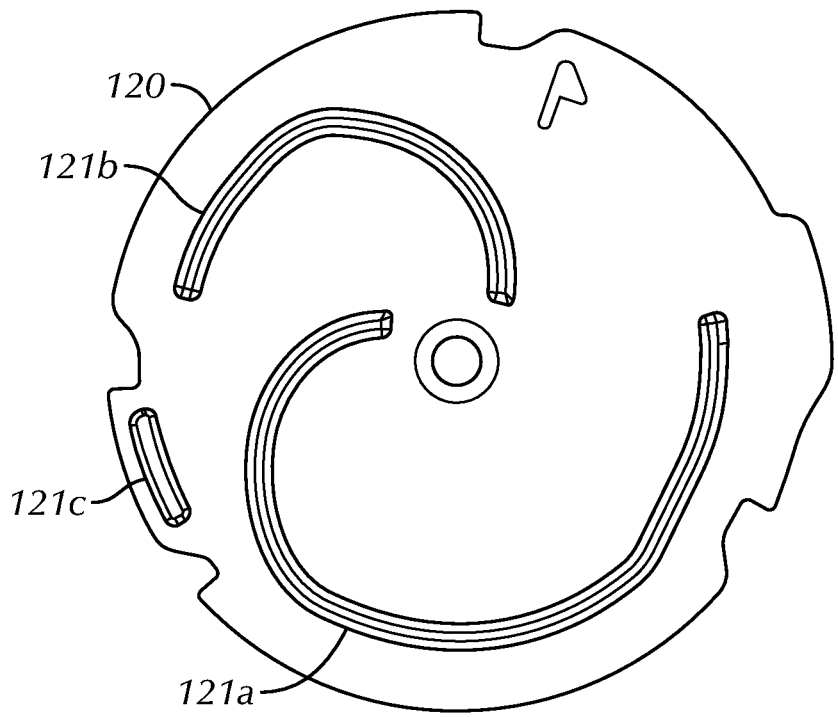
FIG. 11A is a view of the left side of a cam wheel within one embodiment of a handle of a system for treating benign prostatic hyperplasia.
Figure 11B:
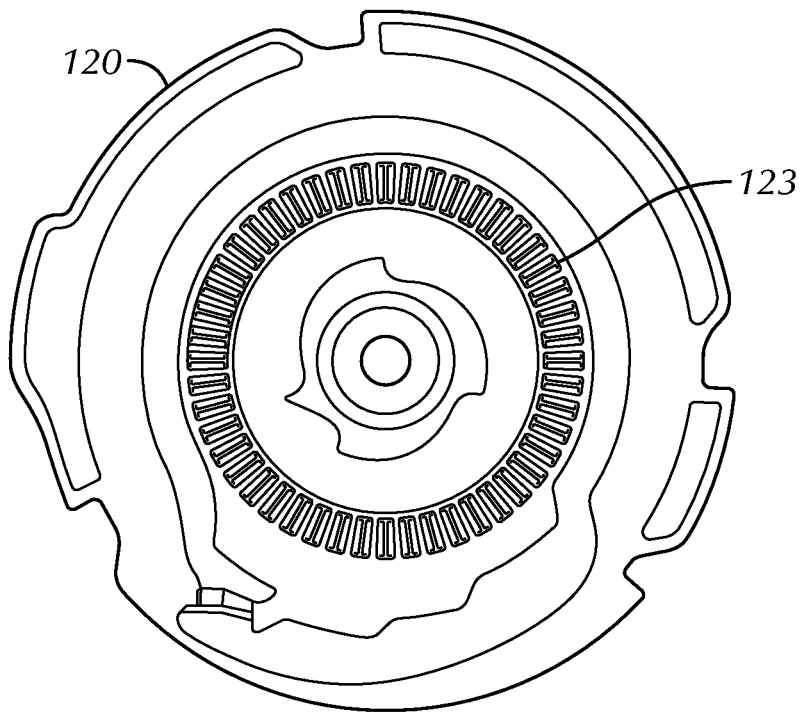
FIG. 11B is a view of the right side of a cam wheel within one embodiment of a handle of a system for treating benign prostatic hyperplasia.

FIGS. 11A and 11B are side views of a cam wheel within one embodiment of a handle of a system for treating benign prostatic hyperplasia. The cam wheel 120 is mounted on an axle molded into the right handle case. The left side of the cam wheel 120, shown in FIG. 11A, includes raised features 121a, 121b, and 121c. The raised features 121a, 121b, and 121c interact with other mechanisms in the handle (such as the various sleds) to facilitate the motion of the various assemblies in the cartridge (such as the needle assembly, suture assembly, pusher assembly, and cutter assembly). The right side of the cam wheel 120, shown in FIG. 11B, includes cam wheel gear teeth 123, which interact with the drive gear 113 (pictured in FIG. 9) to transmit the generally linear motion from squeezing the handle trigger assembly 110 to the circular motion of the cam wheel 120.

Figures 12A, 12B:
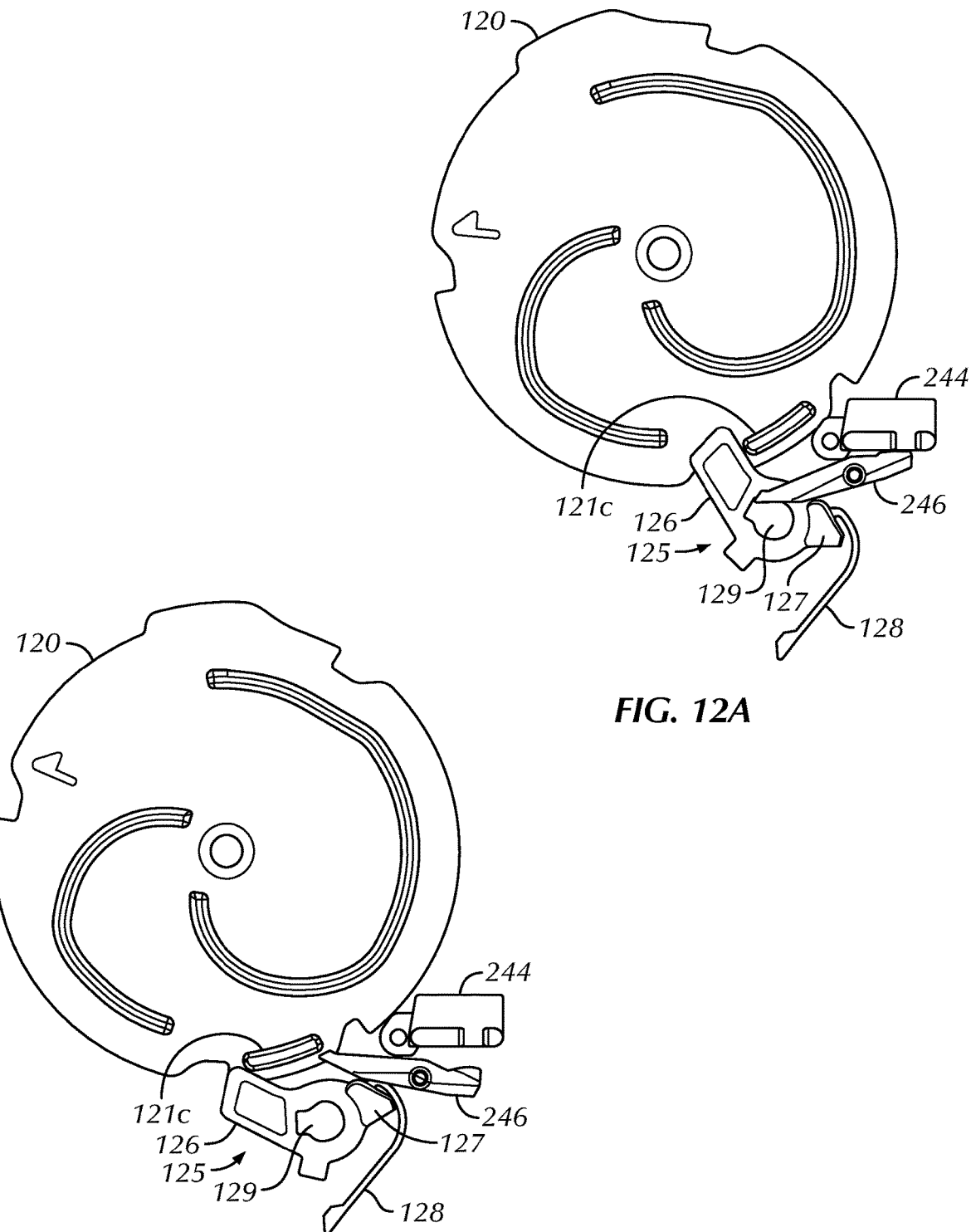
FIG. 12A is a view of the left side of a cam wheel and certain other mechanical features within one embodiment of a handle and cartridge of a system for treating benign prostatic hyperplasia.
FIG. 12B is a view of the left side of a cam wheel and certain other mechanical features within one embodiment of a handle and cartridge of a system for treating benign prostatic hyperplasia.

FIG. 12A is a view of the left side of a cam wheel and certain other mechanical features within one embodiment of a handle and cartridge of a system for treating benign prostatic hyperplasia. FIG. 12B is the same view as FIG. 12A with the cam wheel and other mechanical features in a different configuration than shown in FIG. 12A. In this embodiment the raised feature 121c on the cam wheel 120 is designed to interact with the wheel actuator 125 to release the pusher block 244 and then allow the wheel actuator 125 to be reset. When the cam wheel 120 rotates as a consequence of the user squeezing the handle trigger assembly, the raised feature 121c pushes against a wheel actuator head portion 126 causing the wheel actuator 125 to pivot about the wheel actuator axis 129. As the wheel actuator 125 pivots, the wheel actuator tail portion 127 interacts with the implant actuator 246 causing the implant actuator 246 to pivot. When the implant actuator 246 pivots, the pusher block 244 is released from a held position and allowed to move distally and push the proximal anchor component onto the suture as described elsewhere herein. Further rotation of the cam wheel 120 moves the raised feature 121c entirely past the wheel actuator head portion 126 such that the wheel actuator 125 can pivot back into its original position. The force necessary for returning the wheel actuator 125 to its original position is supplied by the wheel actuator flexure 128, which is flexed against the handle case during the pivot of the wheel actuator 125. Flexing the wheel actuator flexure 128 stores spring energy that is released to move the wheel actuator 125 back to its original position when the wheel actuator head portion 126 is clear of the raised feature 121c. The wheel actuator 125 is thus reset to be able to interact with the implant actuator 246 of the next cartridge that is mechanically engaged with the handle.

The implant actuator 246 and the pusher block 244 (as well as the proximal anchor component and the suture) are present in the cartridge while the cam wheel 120 and the wheel actuator 125 are present in the handle. FIGS. 12A and 12B illustrate the operation of these features when the cartridge and handle are mechanically engaged as described elsewhere herein. For clarity, other features are not pictured in FIGS. 12A and 12B but certain of those features are illustrated in FIGS. 13A and 13B.

Figure 13A:
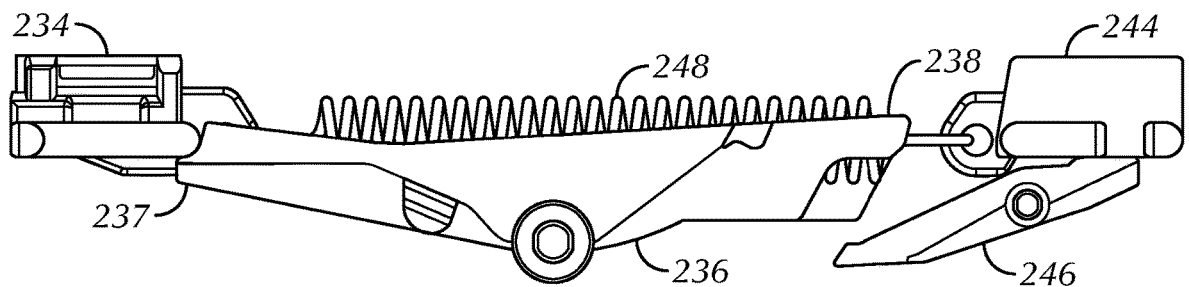
FIG. 13A is a side view of certain mechanical features within one embodiment of a cartridge of a system for treating benign prostatic hyperplasia.
Figure 13B:
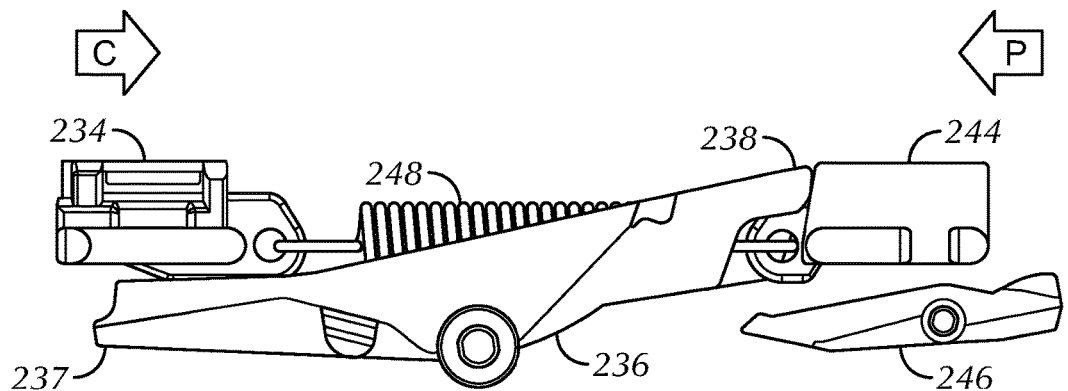
FIG. 13B is a side view of certain mechanical features within one embodiment of a cartridge of a system for treating benign prostatic hyperplasia.

FIG. 13A is a side view of certain mechanical features within one embodiment of a cartridge of a system for treating benign prostatic hyperplasia. FIG. 13B is the same view as FIG. 13A with the mechanical features in a different configuration than shown in FIG. 13A. The pusher block 244 is coupled to the cutter block 234 by the implant spring 248. Both the pusher block 244 and the cutter block 234 are constrained to move linearly along the long axis of the cartridge by the cartridge base 298 and shaft support 297 (each pictured in FIG. 10) that define the cartridge body. The implant spring 248 is an extension spring stretched between the pusher block 244 and the cutter block 234 and exerting a force that tends to draw the pusher block 244 and the cutter block 234 toward each other. The implant actuator 246 prevents the pusher block 244 from moving under the force of the implant spring 248 when the implant actuator 246 is in the configuration depicted in FIG. 13A (and FIG. 12A). The cutter pawl distal end 237 prevents the cutter block 234 from moving under the force of the implant spring 248 when the cutter pawl 236 is in the configuration depicted in FIG. 13A. When the implant actuator 246 is made to pivot as described herein with respect to FIGS. 12A and 12B, the pusher block 244 moves distally (i.e., the pusher assembly moves in the direction of arrow "P") to push the proximal anchor component onto the suture as described elsewhere herein. During this motion, which is driven by the force of the implant spring 248, the pusher block 244 interacts with the cutter pawl proximal end 238 and causes the cutter pawl 236 to pivot as depicted in FIG. 13B. The sloped front surface of the pusher block 244 and the curved surface of the cutter pawl proximal end 238 interact to create this pivoting motion. When the cutter pawl 236 pivots, the cutter pawl distal end 237 disengages from the cutter block 234 and allows the cutter block 234 to move proximally under the force of implant spring 248. The proximal motion of the cutter block 234 causes the suture to be cut to form the suture portion of the anchor assembly. That is, the cutter assembly moves in the direction of arrow "C" to complete the anchor assembly and detach it from the cartridge and handle system.

As described elsewhere herein, in some embodiments multiple cartridges can be used in serial fashion with a single handle. The steps and mechanisms illustrated and explained with respect to FIGS. 12A, 12B, 13A, and 13B disclose how the pushing and cutting steps of creating the anchor assembly can be repeatedly executed for multiple engagements of a series of cartridges with a single handle. One notable feature is that the implant spring is in an extended state as its initial condition. It is important, then, for the cartridge to have features that prevent the unintended release of the energy in the implant spring during handling of the cartridge.

Figure 14:
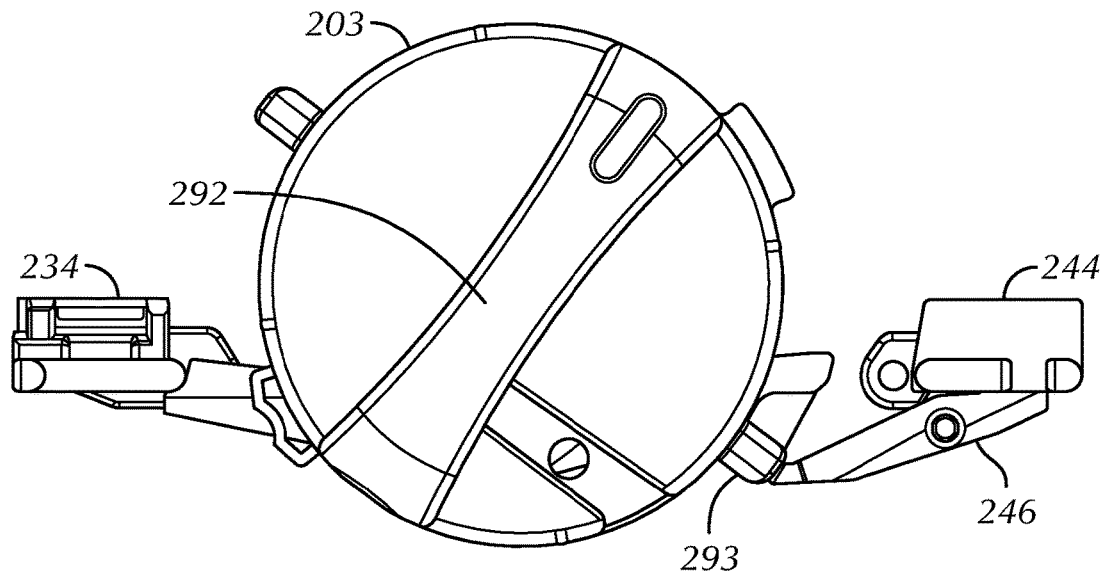
FIG. 14 is a side view of certain mechanical features within one embodiment of a cartridge of a system for treating benign prostatic hyperplasia.

FIG. 14 is a side view of certain mechanical features within one embodiment of a cartridge of a system for treating benign prostatic hyperplasia. FIG. 14 illustrates the mechanisms depicted in FIG. 13A (in the configuration of FIG. 13A) with the addition of the cartridge knob 203 to show the operational relationship among these features. FIG. 14 illustrates the cartridge knob 203 in the storage position. In the storage position, the grip section 292 is transverse to the long axis of the cartridge as compared to the engaged position shown in FIG. 1 in which the grip section 292 is aligned with the long axis of the cartridge. When in the storage position, the cartridge knob 203 functions as a safety interlock that prevents movement by the pusher block 244. In the storage position depicted in FIG. 14, a pusher safety tab 293 on the cartridge knob 203 engages with the distal end of the implant actuator 246 and prevents the implant actuator 246 from pivoting to release the pusher block 244 (as illustrated and explained with respect to FIGS. 12A and 12B). The pusher safety tab 293 allows the cartridge to be safely handled and stored while the implant spring is in its extended configuration.

Figure 15A:
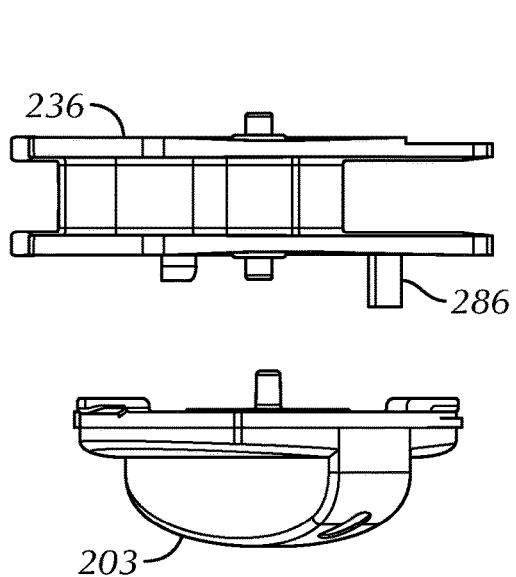
FIG. 15A is an exploded, top view of certain mechanical features within one embodiment of a cartridge of a system for treating benign prostatic hyperplasia.
Figure 15B:
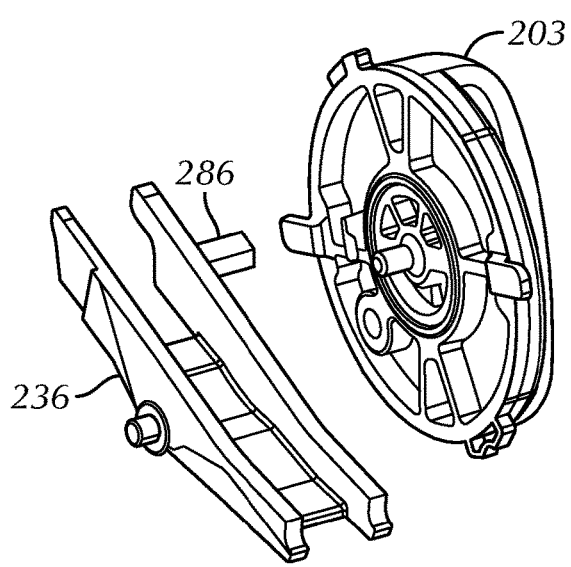
FIG. 15B is an exploded, perspective view of certain mechanical features within one embodiment of a cartridge of a system for treating benign prostatic hyperplasia.

FIG. 15A is an exploded top view of certain mechanical features within one embodiment of a cartridge of a system for treating benign prostatic hyperplasia and 15B is an exploded perspective view of the same features. FIGS. 15A and 15B illustrate another safety interlock in which a cutter safety tab 286 is present on the cutter pawl 236. The cutter safety tab 286 engages with the cartridge knob 203 when the cartridge knob 203 is in the storage position and prevents the cutter pawl 236 from pivoting to release the cutter block (as illustrated and explained with respect to FIGS. 13A and 13B). The cutter safety tab 286 allows the cartridge to be safely handled and stored while the implant spring is in its extended configuration. FIGS. 15A and 15B are illustrated in an exploded view to make the relevant features clear. However, in operation the cutter pawl 236 is closely engaged with the cartridge knob 203 to create the mechanical interactions described herein.

The pusher safety tab 293 and the cutter safety tab 286 solve the problem of accidental firing of the pusher assembly and/or cutter assembly in the cartridge by correlating safety interlocks with the storage position of the cartridge knob 203.

Figures 16A, 16B:
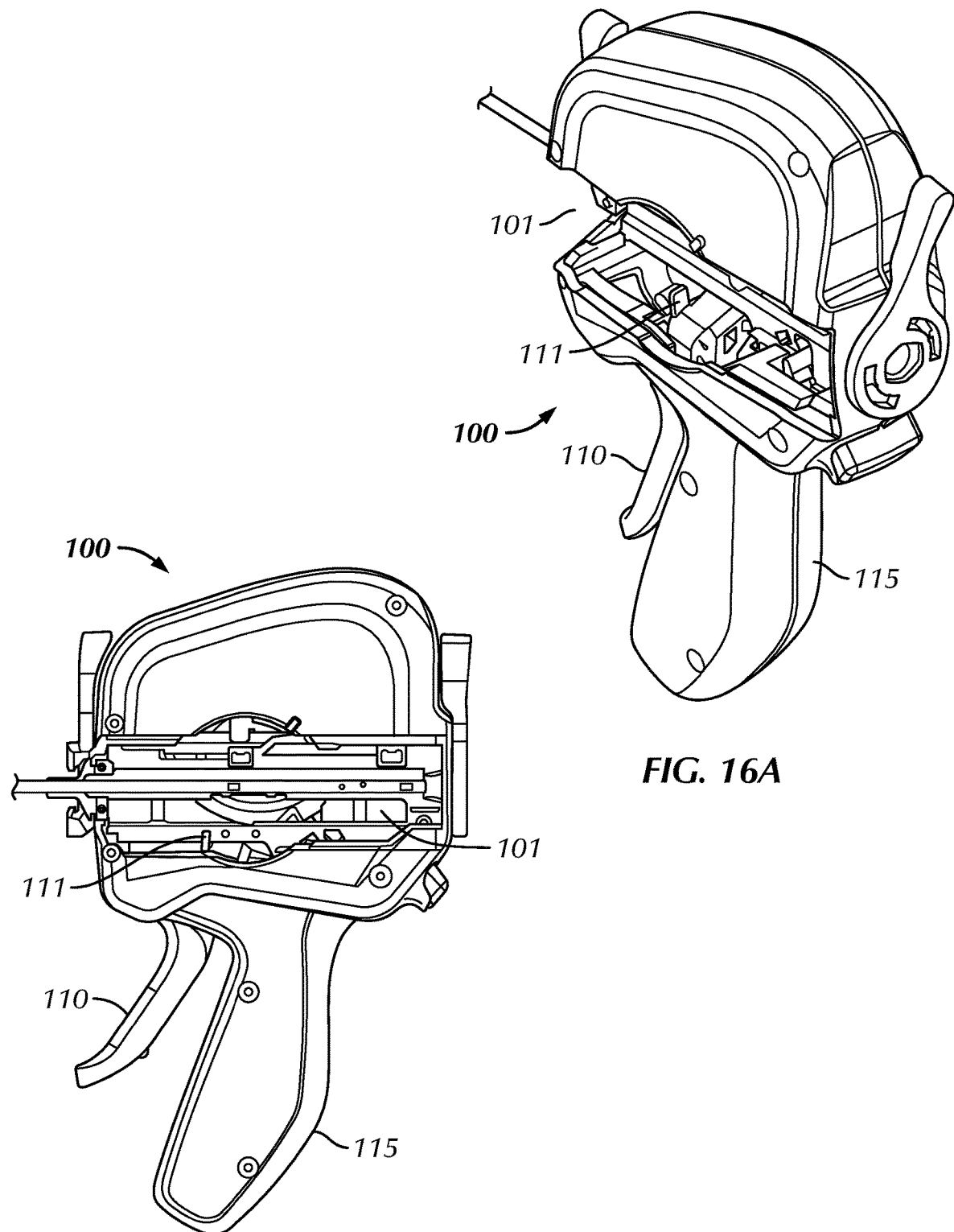
FIG. 16A is a perspective view of a portion of a handle of one embodiment of a system for treating benign prostatic hyperplasia in which the cartridge has been removed.
FIG. 16B is a side view of a portion of a handle of one embodiment of a system for treating benign prostatic hyperplasia in which the cartridge has been removed.

FIGS. 16A, 16B, 17, 18A, and 18B illustrate an embodiment of another safety interlock mechanism in the handle and cartridge system. FIG. 16A is a perspective view of a portion of a handle 100 and FIG. 16B is a side view of the handle 100. The handle 100 includes a cartridge bay 101, which is shown as empty because the cartridge has been removed. In this embodiment, the handle trigger assembly 110 includes cartridge lock tab 111 that protrudes into the cartridge bay 101 when the handle trigger assembly 110 pivots away from the handle grip 115. The presence of the cartridge lock tab 111 in the cartridge bay 101 prevents a cartridge from being engaged with the handle 100 because a cartridge cannot physically fit in the cartridge bay 101 with the cartridge lock tab 111 in the cartridge bay 101. This mechanism prevents a cartridge from being inserted into the handle except under the proper condition—when the handle trigger assembly 110 is in its initial position closest to the handle grip 115. This initial position corresponds with the mechanisms in the handle all being reset to their initial positions.

Figure 17:
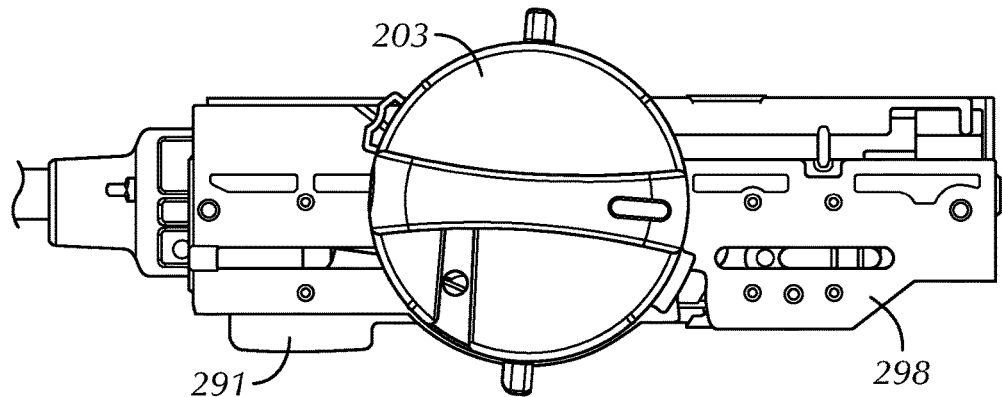
FIG. 17 is a side view of a portion of a cartridge of one embodiment of a system for treating benign prostatic hyperplasia.

FIG. 17 is a side view of a portion of a cartridge of one embodiment of a system for treating benign prostatic hyperplasia. In FIG. 17, the cartridge cover has been removed, revealing the cartridge base 298. The cartridge knob 203 is also shown. A cartridge lock surface 291 is present on the shaft support 297 and extends below the cartridge base 298 in this side view of a portion of a cartridge.

Figure 18A:
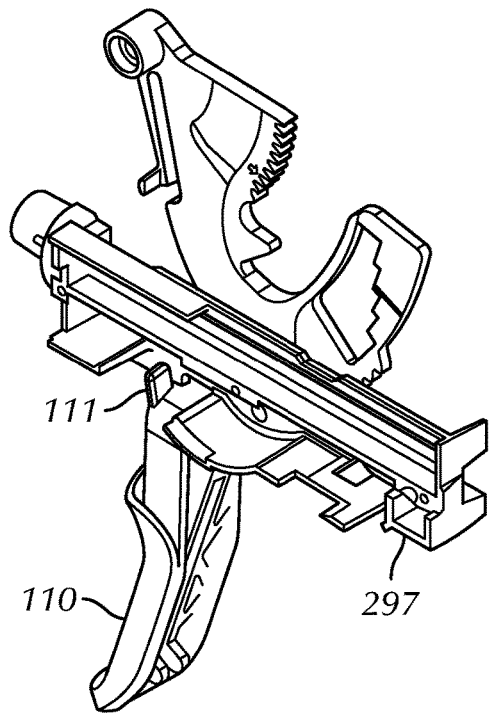
FIG. 18A is a perspective view of certain mechanical features within one embodiment of a cartridge of a system for treating benign prostatic hyperplasia.
Figure 18B:
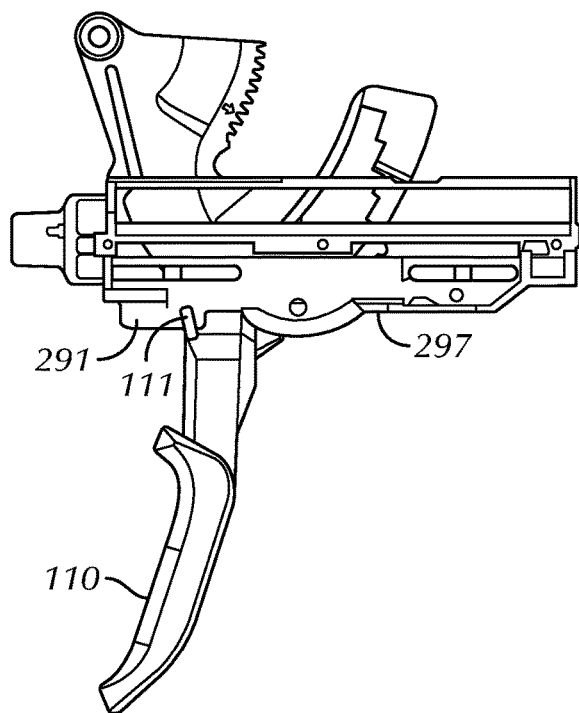
FIG. 18B is a side view of certain mechanical features within one embodiment of a cartridge of a system for treating benign prostatic hyperplasia.

FIGS. 18A and 18B are a perspective view and a side view, respectively, of certain mechanical features within one embodiment of a cartridge of a system for treating benign prostatic hyperplasia. FIGS. 18A and 18B illustrate the interaction between the cartridge lock tab 111 present on the handle trigger assembly 110 and the cartridge lock surface 291 present on the shaft support 297. When the handle trigger assembly 110 is in a position pivoted away from the handle grip, the cartridge lock tab 111 prevents the cartridge from being removed from the cartridge bay by physically impeding the removal of the cartridge. While the cartridge lock surface 291 is present on the shaft support 297 in this embodiment, a similar lock surface could be present on other parts of the cartridge, such as the cartridge base 298, and function in a substantially similar manner. The cartridge lock tab 111 present on the handle trigger assembly 110 provides a method of preventing insertion of a cartridge until the handle is in the reset, initial condition, and prevents removal of a cartridge (via interaction with the cartridge lock surface 291) while the handle and cartridge system is in use. There are alternative embodiments for preventing removal and/or insertion of a cartridge. For example, a cartridge may contain a lock receiving feature and the handle may contain an additional wheel with a series of locking features. As the handle trigger is pulled, the additional wheel rotates such that a locking feature engages the lock receiver. If a complete cycle for implantation requires multiple trigger squeezes, then the additional wheel includes sufficient locking features to keep the cartridge locked in during the entire cycle. At the end of the cycle, a portion of the additional wheel containing no locking feature is aligned with the lock receiver. In this way, the cartridge would be unlocked and removable from the handle. As another example, a locking slide could be engaged by a user to lock the cartridge in the handle. When the trigger is squeezed, the slide would be mechanically engaged to prevent the slide from moving until the cycle was completed.

Figure 19A:
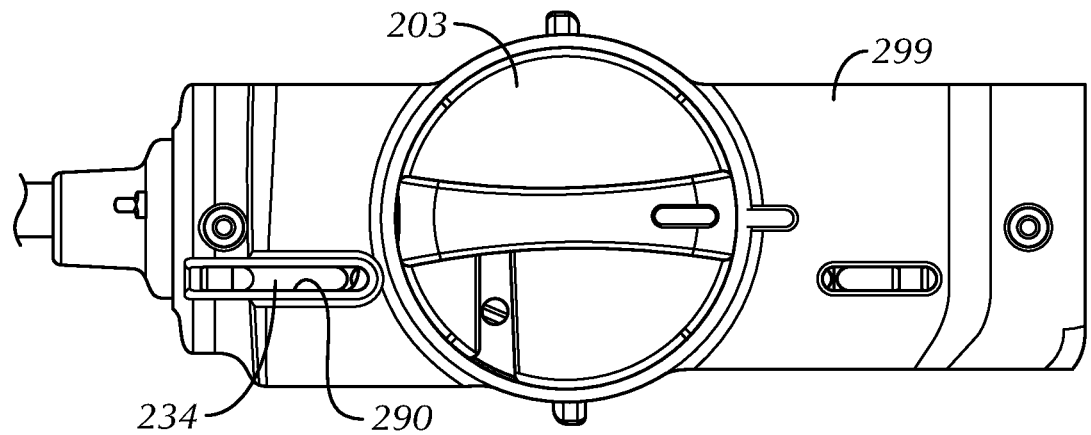
FIG. 19A is a side view of a portion of a cartridge of one embodiment of a system for treating benign prostatic hyperplasia.
Figure 19B:
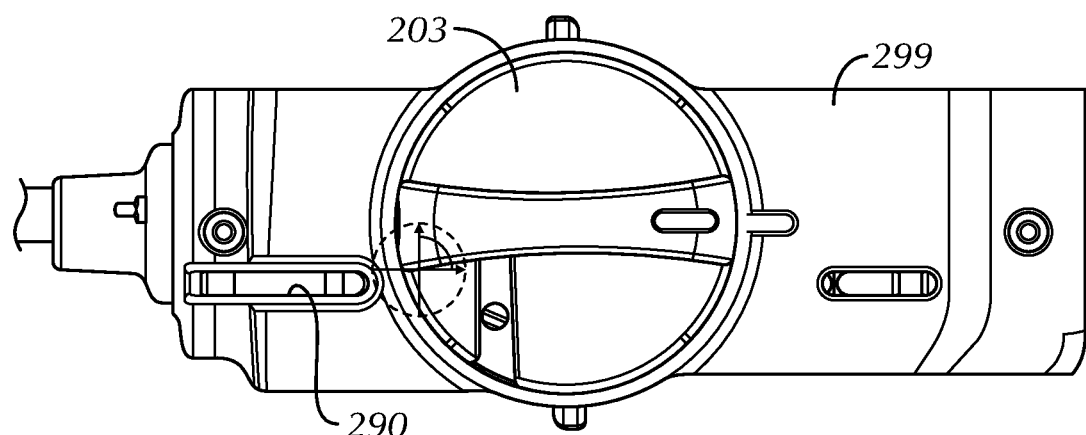
FIG. 19B is a side view of a portion of a cartridge of one embodiment of a system for treating benign prostatic hyperplasia.

FIGS. 19A and 19B are side views of a portion of a cartridge of one embodiment of a system for treating benign prostatic hyperplasia. The cartridge knob 203 is engaged with the cartridge cover 299, which includes a cartridge indicator window 290. In FIG. 19A, the cutter block 234 is visible through the cartridge indicator window 290, which indicates that the cutter block 234 is still in its initial position and has not moved proximally to cut the suture in the final step of the formation of the anchor assembly. FIG. 19A shows that the cutter block 234 fills the cartridge indicator window 290. In FIG. 19B, only a small portion of the cutter block 234 is visible through the cartridge indicator window 290. That is, the cutter block 234 no longer fills the cartridge indicator window 290. This indicates that the cutter block 234 has moved proximally and cut the suture for the final step of the formation of the anchor assembly.

Figure 19C:
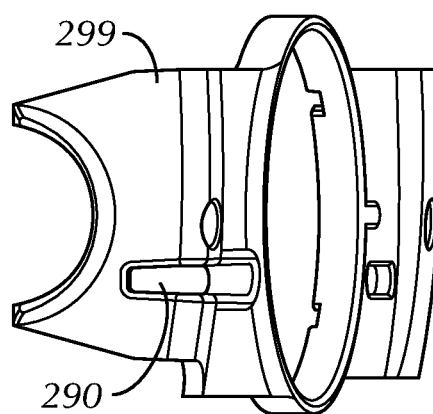
FIG. 19C is a perspective view of a cartridge cover of one embodiment of a system for treating benign prostatic hyperplasia.

FIG. 19C is a perspective view of a cartridge cover of one embodiment of a system for treating benign prostatic hyperplasia. FIG. 19C illustrates that the cartridge indicator window 290 is cut through the distal surface of the cartridge cover 299. The cartridge indicator window 290 is able to perform an additional function of providing access to the cutter block 234 such that a user can use a small tool to move the cutter block distally to cut the suture if the cutter block 234 stalls and does not completely cut the suture. The presence of an opening to the cartridge indicator window 290 through the distal surface of the cartridge cover 299 allows for easy access to the cutter block 234 with a tool, even when the user is not looking directly at the cartridge indicator window 290.

Figure 20A:
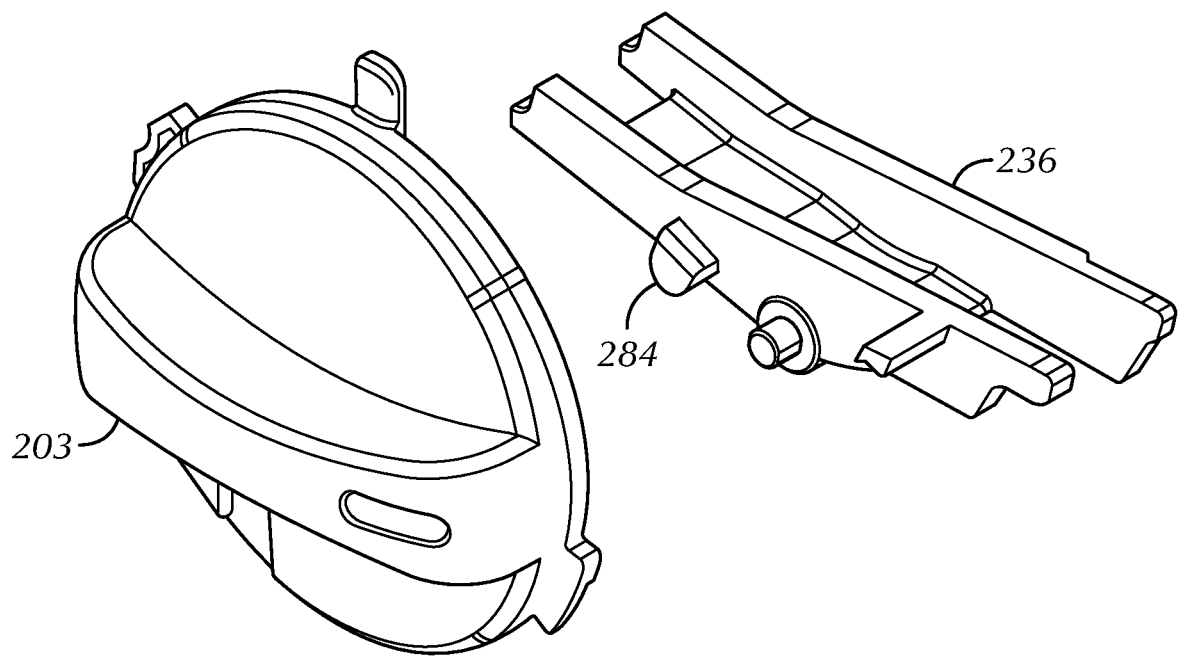
FIG. 20A is an exploded perspective view of certain mechanical features within one embodiment of a cartridge of a system for treating benign prostatic hyperplasia.
Figure 20B:
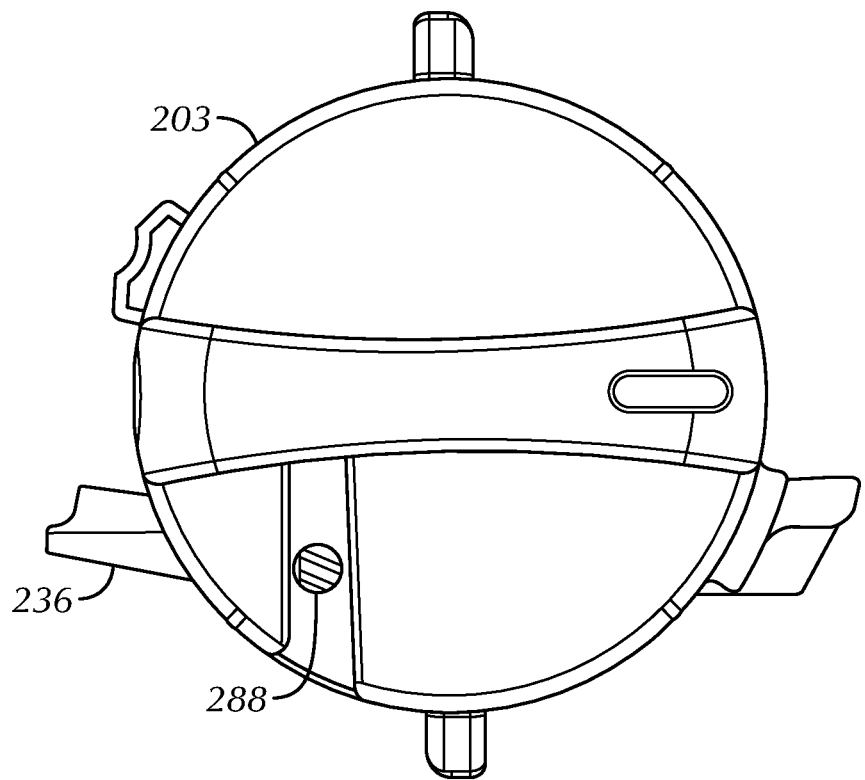
FIG. 20B is a side view of certain mechanical features within one embodiment of a cartridge of a system for treating benign prostatic hyperplasia.

FIG. 20A is an exploded perspective view of certain mechanical features within one embodiment of a cartridge of a system for treating benign prostatic hyperplasia and FIG. 20B is a side view of those mechanical features in their engaged configuration. As described herein with respect to FIGS. 13A and 13B, in normal operation the cutter pawl 236 pivots and disengages from the cutter block allowing the cutter block to move proximally under the force of the implant spring. The proximal motion of the cutter block causes the suture to be cut to form the suture portion of the anchor assembly. However, in some circumstances it may be desirable for a user to interrupt the deployment sequence after deployment of the distal anchor component but prior to the deployment of the proximal anchor component and cutting of the suture. In such a circumstance, the handle and cartridge system can then be removed from the patient without completely assembling and deploying the implant.

FIGS. 20A and 20B illustrate that the cutter pawl 236 includes a cutter manual tab 284 that is accessible to a user via a cutter access window 288 present on the cartridge knob 203. The cutter manual tab 284 is configured as an off-center ramp such that pushing on the cutter manual tab 284 through the cutter access window 288 creates rotation (or pivoting) of the cutter pawl 236 perpendicular to the push direction. A user can push the cutter manual tab 284 with a small tool inserted through the cutter access window 288. Indentations in the cartridge knob 203 near the cutter access window 288 guide the tool towards the cutter access window 288. As described herein, this pivoting of the cutter pawl 236 disengages the cutter pawl from the cutter block and allows the cutter block to move proximally under the force of the implant spring to cut the suture.

The disclosed apparatus can be implemented in various treatment devices employed for various medical purposes including, but not limited to, retracting, lifting, compressing, approximating, supporting, remodeling, repositioning, ablating, or otherwise altering tissues, organs, anatomical structures, grafts, or other material found within the body of a human or animal subject. In certain embodiments, treatment devices are intended to displace, compress, retract, or destroy tissue of the prostate to facilitate treatment of diseases or disorders such as BPH.

Other treatment devices may benefit from the use of the embodiments disclosed herein. Treatment devices equipped with various tools which manipulate, ablate, or otherwise alter tissue, where those tools are moved, deployed, or driven by mechanical energy, can benefit from the use of the safety interlocks and mechanisms, as well as the use of the deployment indicators, disclosed herein. Such tools can include, but are not limited to, needles, cutting blades, vacuums, grasping arm assemblies, expandable cutting members, blunt dissectors, noose or ligature clips, articulating heads with an integral or retractable blade, helical blades, electrodes for delivery of radiofrequency energy, cutting wires or rings, electrocauterizing probes, or staple or suture delivery heads.

In some embodiments, the system includes a cartridge carrying at least one implant and a handle configured to receive the cartridge. The handle includes an actuator and at least one spring mechanism loaded with mechanical energy. The handle also includes a member that mates with the cartridge to transfer mechanical energy from the spring mechanism to the cartridge for deploying the implant. The handle and cartridge system includes a first firing sled that has slots aligning with pusher tabs on a needle assembly. The slots of the first firing sled and the pusher tabs of the needle assembly are complementary mechanisms that allow for the transfer of energy from the spring mechanism via the first firing sled to fire a needle in the cartridge. The handle and cartridge system can also include a second firing sled with slots aligning with pusher tabs on a suture tube or connector tube. The slots of the second firing sled and the pusher tabs of the suture tube are complementary mechanisms that allow for the transfer of energy from the spring mechanism via the second firing sled to advance the suture tube simultaneously with the needle tube.

While particular elements, embodiments and applications of the present invention have been shown and described, it will be understood that the invention is not limited thereto since modifications can be made by those skilled in the art without departing from the scope of the present disclosure, particularly in light of the foregoing teachings.

Table of Reference Numerals

| | |
|---|---|
| 1 | system |
| 70 | distal anchor component |
| 72 | head portion |
| 74 | tail portion |
| 78 | suture portion |
| 80 | mid-section |
| 82 | connector section |
| 84 | proximal anchor component |
| 95 | back end |
| 96 | prong |
| 98 | tab |
| 100 | handle |
| 101 | cartridge bay |
| 102 | scope tube |
| 103 | right handle case |
| 104 | left handle case |
| 105 | scope seal |
| 110 | handle trigger assembly |
| 111 | cartridge lock tab |
| 112 | safety |
| 113 | drive gear |
| 114 | ratchet |
| 115 | handle grip |
| 120 | cam wheel |
| 125 | wheel actuator |
| 126 | wheel actuator head portion |
| 127 | wheel actuator tail portion |
| 128 | wheel actuator flexure |
| 129 | wheel actuator axis |
| 130 | cover plate |

-continued

Table of Reference Numerals

| | |
|---|---|
| 140 | needle sled |
| 145 | axle |
| 150 | suture sled |
| 160 | implant sled |
| 170 | scope lock |
| 180 | sheath lock |
| 200 | cartridge |
| 201 | cartridge body |
| 202 | shaft assembly |
| 203 | cartridge knob |
| 204 | shaft distal portion |
| 205 | shaft distal portion exit port |
| 206 | shaft distal portion cutout |
| 207 | shaft distal portion lumen |
| 208 | shaft distal portion interior exit wall |
| 209 | shaft distal portion upper cutout |
| 210 | needle assembly |
| 212 | needle distal portion |
| 214 | needle shaft |
| 216 | needle proximal portion |
| 220 | suture assembly |
| 222 | suture |
| 224 | suture support tube |
| 226 | suture safety |
| 228 | suture proximal portion |
| 230 | cutter assembly |
| 232 | cutter |
| 234 | cutter block |
| 236 | cutter pawl |
| 237 | cutter pawl distal end |
| 238 | cutter pawl proximal end |
| 240 | pusher assembly |
| 242 | pusher |
| 244 | pusher block |
| 246 | implant actuator |
| 248 | implant spring |
| 284 | cutter manual tab |
| 286 | cutter safety tab |
| 288 | cutter access window |
| 290 | cartridge indicator window |
| 291 | cartridge lock surface |
| 292 | grip section |
| 293 | pusher safety tab |
| 296 | atraumatic tape |
| 297 | shaft support |
| 298 | cartridge base |
| 299 | cartridge cover |

We claim:

1. A cartridge for a system that includes a handle and the cartridge, where the handle is configured to accept a series of such cartridges and impart mechanical energy to the cartridge to deliver an implant, comprising:

a cartridge body coupled to a shaft assembly having a long axis;

a distal portion of the shaft assembly having a lumen running through the distal portion, the lumen having a lumen radius of curvature defined by a distal lumen wall and the curving of the lumen as it runs in a first direction parallel to the long axis to a second direction transverse to the long axis;

a needle assembly slidably disposed within the shaft assembly and the cartridge body and having a needle defining a needle distal portion such that the needle distal portion is configured to exit the shaft assembly from an exit port at which the lumen terminates, the needle distal portion having a needle radius of curvature defined by the curving of the needle as it runs in a first direction parallel to the long axis to run in a second direction transverse to the long axis, where the lumen radius of curvature and the needle radius of curvature are different; and a cutout on the shaft assembly located at least partially proximal to the exit port through which the needle distal portion is configured to exit, the cutout comprising an opening between the lumen and an exterior of the shaft configured to allow at least part of the needle distal portion to flex therethrough.

2. The cartridge of claim 1, wherein the distal lumen wall comprises a partial exit wall and a second cutout.

3. The cartridge of claim 1, wherein the distal lumen wall is curved.

4. The cartridge of claim 1, wherein at least a portion of the distal lumen wall is straight.

* * * * *